(12) United States Patent
Beeharry et al.

(10) Patent No.: US 10,799,508 B2
(45) Date of Patent: Oct. 13, 2020

(54) METHODS FOR TREATING CANCER USING HSP90 INHIBITORS

(71) Applicant: AI Therapeutics, Inc., Guilford, CT (US)

(72) Inventors: Neil Beeharry, Guilford, CT (US); Marylens Hernandez, Guilford, CT (US); Sean Landrette, Meriden, CT (US); Tian Xu, Guilford, CT (US); Jonathan M. Rothberg, Guilford, CT (US); Henri Lichenstein, Guilford, CT (US)

(73) Assignee: A1 Therapeutics, Inc., Guilford, CT (US)

( * ) Notice: Subject to any disclaimer, the term of this patent is extended or adjusted under 35 U.S.C. 154(b) by 0 days.

(21) Appl. No.: 15/885,975

(22) Filed: Feb. 1, 2018

(65) Prior Publication Data

US 2018/0221376 A1 Aug. 9, 2018

Related U.S. Application Data

(60) Provisional application No. 62/454,113, filed on Feb. 3, 2017, provisional application No. 62/563,991, filed on Sep. 27, 2017, provisional application No. 62/587,886, filed on Nov. 17, 2017.

(51) Int. Cl.
| | |
|---|---|
| *A61K 31/52* | (2006.01) |
| *A61K 31/496* | (2006.01) |
| *A61K 31/437* | (2006.01) |
| *A61K 31/46* | (2006.01) |
| *A61P 35/02* | (2006.01) |
| *A61K 31/416* | (2006.01) |
| *A61P 35/00* | (2006.01) |
| *A61K 31/444* | (2006.01) |
| *A61K 31/635* | (2006.01) |
| *A61K 31/395* | (2006.01) |
| *A61K 45/06* | (2006.01) |

(52) U.S. Cl.
CPC .......... *A61K 31/52* (2013.01); *A61K 31/395* (2013.01); *A61K 31/416* (2013.01); *A61K 31/437* (2013.01); *A61K 31/444* (2013.01); *A61K 31/46* (2013.01); *A61K 31/496* (2013.01); *A61K 31/635* (2013.01); *A61K 45/06* (2013.01); *A61P 35/00* (2018.01); *A61P 35/02* (2018.01); *A61K 2300/00* (2013.01)

(58) Field of Classification Search
None
See application file for complete search history.

(56) References Cited

U.S. PATENT DOCUMENTS

| | | |
|---|---|---|
| 2014/0315929 A1 | 10/2014 | Chiosis |
| 2019/0091229 A1 | 3/2019 | Lichenstein et al. |

FOREIGN PATENT DOCUMENTS

| | | | |
|---|---|---|---|
| WO | WO-2011/060253 A2 | 5/2011 | |
| WO | 2012148550 A1 | 11/2012 | |
| WO | WO-2012/148550 A1 | 11/2012 | |
| WO | WO-2012148550 A1 * | 11/2012 | .......... C07D 473/34 |
| WO | 2018144680 A1 | 8/2018 | |
| WO | 2019067666 A1 | 4/2019 | |
| WO | WO-2019/067666 A1 | 4/2019 | |

OTHER PUBLICATIONS

Wainberg et al., "Inhibition of HSP90 with AUY922 induces synergy in HER2 amplified trastuzumab resistant breast and gastric cancer," American Association for Cancer Research published Feb. 8, 2013.*
Millela et al., Trastuzumab down-regulates Bcl-2 expression and potentiates apoptosis induction by Bcl-2/Bcl-XL bispecific antisense oligonucleotides in HER-2 gene—amplified breast cancer cells, Clin Cancer Res. Nov. 15, 2004; 10(22):7747-56.*
Pan et al., "Selective BCL-2 Inhibition by ABT-199 Causes on Target Cell Death in Acute Myeloid Leukemia," Cancer Discov. Mar. 2014; 4(3): 362-375.*
Fennell et al., "Circumventing HSP90 inhibitors via apoptosis block," Oncoscience 2015, vol. 2, No. 9.*
Nayar et al., "Targeting the Hsp90-associated viral oncoproteome in gammaherpesvirus-associated malignancies," Blood, Oct. 17, 2013, vol. 122, No. 16.*
Trendowski, "PU-H71: An improvement on nature's solutions to oncogeneic Hsp90 addiction," Pharmacological Research 99 (2015) 202-216.*
Bae, J. et al. (Jun. 15, 2007). "Phenotypic and functional effects of heat shock protein 90 inhibition on dendritic cell," *J Immunol* 178(12):7730-7737.
Bae, J. et al. (Feb. 1, 2013, e-published Jan. 4, 2013). "Heat shock protein 90 is critical for regulation of phenotype and functional activity of human T lymphocytes and NK cells," *J Immunol* 190(3):1360-1371.
Berthon, C. et al. (Dec. 2010, e-published Sep. 4, 2010). "In acute myeloid leukemia, B7-H1 (PD-L1) protection of blasts from cytotoxic T cells is induced by TLR ligands and interferon-gamma and can be reversed using MEK inhibitors," *Cancer Immunol Immunolther* 59(12):1839-1849.
Bhat, R. et al. (Nov. 13, 2014, e-published Aug. 29, 2014). "Progress in the discovery and development of heat shock protein 90 (Hsp90) inhibitors," *J Med Chem* 57(21):8718-8728.

(Continued)

*Primary Examiner* — Jared Barsky
(74) *Attorney, Agent, or Firm* — Muriel Liberto, Esq.; Mintz Levin Cohn Ferris Glovsky and Popeo, P.C.

(57) ABSTRACT

The disclosure also provides compositions and methods related to combination therapy with HSP90 inhibitors and BCL-2 pathway inhibitors for treating cancer. The disclosure also provides compositions and methods related to the use of 'low dose' HSP90 inhibitors in the treatment of cancer, alone and in combination with other therapeutic agents.

12 Claims, 17 Drawing Sheets

(56) References Cited

OTHER PUBLICATIONS

Blatt, K. et al. (Oct. 4, 2016). "Evaluation of in vitro effects of various targeted drugs on plasma cells and putative neoplastic stem cells in patients with multiple myeloma," *Oncotarget* 7(40):65627-65642.

Busacca, S. et al. (Mar. 24, 2016, e-published Jun. 22, 2015). "Resistance to HSP90 inhibition involving loss of MCL1 addiction," *Oncogene* 35(12):1483-1492.

Cang, S. et al. (Nov. 20, 2015). "ABT-199 (venetoclax) and BCL-2 inhibitors in clinical development," *J Hematol Oncol* 8:129.

Chen, X. et al. (May 2008). "Clinical significance of B7-H1 (PD-L1) expression in human acute leukemia," *Cancer Biol Ther* 7(5):622-627.

Jayanthan, A. et al. (Jul. 2009). "Targeting the Bcl-2 family of proteins in Hodgkin lymphoma: in vitro cytotoxicity, target modulation and drug combination studies of the Bcl-2 homology 3 mimetic ABT-737," *Leuk Lymphoma* 50(7):1174-1182.

Kronig, H. et al. (Mar. 2014, e-published Nov. 26, 2013). "Interferon-induced programmed death-ligand 1 (PD-L1/B7-H1) expression increases on human acute myeloid leukemia blast cells during treatment," *Eur J Haematol* 92(3):195-203.

Lampson, B.L. et al. (Feb. 2017). "The Development and Current Use of BCL-2 Inhibitors for the Treatment of Chronic Lymphocytic Leukemia," *Cuff Hematol Maliq Rep* 12(1):11-19.

Neckers, L. et al. (Jan. 1, 2012). "Hsp90 molecular chaperone inhibitors: are we there yet?" *Clin Cancer Res* 18(1):64-76.

Pan, R. et al. (Mar. 2014, e-published Dec. 17, 2013). "Selective BCL-2 inhibition by ABT-199 causes on-target cell death in acute myeloid leukemia," *Cancer Discov* 4(3):362-375.

Salih, H.R. et al. (Jul. 2006). "The role of leukemia-derived B7-H1 (PD-L1) in tumor-T-cell interactions in humans," *Exp Hematol* 34(7):888-894.

Tukaj, S. et al. (Apr. 2, 2014). "Inhibitory effects of heat shock protein 90 blockade on proinflammatory human Th1 and Th17 cell subpopulations," *J Inflamm (Lond)* 11(1):10.

Wang, B. et al. (Nov. 2014, e-published Sep. 6, 2014). "Hsp90 inhibitor 17-AAG sensitizes Bcl-2 inhibitor (-)-gossypol by suppressing ERK-mediated protective autophagy and Mcl-1 accumulation in hepatocellular carcinoma cells," *Exp Cell Res* 328(2):379-387.

Partial Search Report dated May 14, 2018, for PCT Application No. PCT/US2018/016361, filed Feb. 1, 2018, 23 pages.

Chou, T-C. (2010). "Drug combination studies and their synergy quantification using the Chou-Talalay method." *Cancer Res.* 70(2): 440-446. DOI: 10.1158/0008-5472.CAN-09-1947. First published Jan. 12, 2010.

Ryan, J. et al. (e-published Apr. 20, 2013). "BH3 profiling in whole cells by fluorimeter or FACS" *Methods* 61(2013):156-164.

Barrott, J. et al., (2013). "Hsp90, an unlikely ally in the war on cancer." *FEBS J.* 280(6):1-24. Doi:10.1111/febs.12147.

Brunelle, J. et al., "Control of mitochondrial apoptosis by the Bcl-2 family." *J. Cell Sci.*122:437-441.

Cohen-Saidon, C. et al., (2006). Antiapoptotic function of Bcl-2 in mast cells is dependent on its association with heat shock protein 90β. *Blood* 107(4):1413-1420.

Fennell, D. et al., (Aug. 20, 2015, e-collection 2015). "Circumventing HSP90 inhibitors via apoptosis block." *Oncoscience* 2(9):747-748.

Goldstein, R. et al., (2015). "Pharmacoproteomics identifies combinatorial therapy targets for diffuse large B cell lymphoma." *J. Clin. Invest.* 125(12):4559-4571. Doi:10.1172/JC180714.

Kamal, A. et al., (Sep. 25, 2003). "A high-affinity conformation of Hsp90 confers tumour selectivity n Hsp90 inhibitors." *Nature* 425(6956):407-410.

Kim, S-H. et al., (Nov. 15, 2015, e-published Sep. 28, 2015). "Discovery of an L-alanine ester prodrug of the Hsp90 inhibitor, MPC-3100." *Bioorg. Med. Chem. Lett.*25(22)52545257.

Milella, M. et al., (Nov. 15, 2004). "Trastuzumab down-regulates Bcl-2 expression and potentiates apoptosis induction by Bcl-2/Bcl-XL bispecific antisense oligonucleotides in HER-2 gene—amplified breast cancer cells." *Clin. Cancer Res.* 10(22):7747-7756.

Montero, J. et al., (2018). "Why do BCL-2 inhibitors work and where should we use them in the clinic?" *Cell Death and Differentiation* 25:56-64.

Moulick, K. et al., (2011). "Affinity-based proteomics reveal cancer-specific networks coordinated by Hsp90." *Nat. Chem. Biol.* 7(11):818-826.

Ritz, C. et al., (2015). "Dose-response analysis using R." *PLOS One* 10(12):e0146021.doi:10.1371/journal.pone.0146021.

Rodina, A. et al., (2016). "The epichaperone is an integrated chaperone network that facilitates tumour survival." *Nature* 538(7625):397-401. Doi:10.1038/nature19807.

Tallarida, R. (2011). "Quantitative methods for assessing drug synergism." *Genes & Cancer* 2(11):1003-1008.

Wainberg, Z. et al., (Feb. 8, 2013). "Inhibition of HSP90 with AUY922 induces synergy in HER2 amplified trastuzumab resistant breast and gastric cancer." *Mol. Cancer Ther.* DOI:10.1158/1535-7163.MCT-12-0507.

Yang, H. et al., (2017). "HSP90 inhibitor (NVP-AUY922) enhances the anti-cancer effect of BCL-2 inhibitor (ABT-737) in small cell lung cancer expressing BCL-2." *Cancer Lett.* 411:19-26.

International Search Report dated Dec. 20, 2018, for PCT Application No. PCT/US2018/053025, filed Sep. 27, 2018, 7 pages.

Written Opinion dated Dec. 20, 2018, for PCT Application No. PCT/US2018/053025, filed Sep. 27, 2018, 10 pages.

ABT-199 (venetoclax) at https://www.chemietek.com/abt-199--venetoclax-details.aspx (2014). (Retrieved from the Internet Jul. 31, 2019).

Fennell, D. et al. (2015). "Circumventing HSP90 inhibitors via apoptosis block." Oncoscience 2(9):747-748.

Millela, M. et al., (2004). "Trastuzumab Down-Regulates Bcl-2 Expression and Potentiates Apoptosis Induction by Bcl-2/Bcl-XL Bispecific Antisense Oligonucleotides in HER-2 Gene—Amplified Breast Cancer Cells." Clinical Cancer Research 10(22):7747-7756.

Nayar, U. et al. (2013). "Targeting the Hsp90-associated Viral Oncoproteome in Gammaherpesvirus-Associated Malignancies." Blood 122(16):2837-2847.

Pan, R. et al. (2014). "Selective BCL-2 Inhibition by ABT-199 Causes On-Target Cell Death in Acute Myeloid Leukemia." Cancer Discovery 4(3):362-375.

Richardson, P. et al., (2012). "Inhibition of heat shock protein 90 (HSP90) as a therapeutic strategy for the treatment of myeloma and other cancers." British Journal of Haematology 152:367-379.

Samlowski, W. et al. (2011). "Phase 1 study of HSP90 inhibitor MPC-3100 in subjects with refractory or recurrent cancer." Molecular Cancer Therapy 10 (Supplement 11) Abstract A96.

Sidera, K., et al., (Jan. 1, 2014). "Current development and potential in cancer therapy." Recent Patents on Anti-Cancer Drug Discovery 9:1-20.

Trendowski, M. (Sep. 2015). "PU-H71: An Improvement on Nature's Solutions to Oncogenic Hsp90 Addiction." Pharmacology Research 99:202-216.

Wainberg, Z. et al. (2013). "Inhibition of HSP90 with AUY922 induces synergy in HER2 amplified trastuzumab resistant breast and gastric cancer." Molecular Cancer Therapeutics 12(4):509-519.

Yao, Q. et al., (2005). "Human leukemias with mutated FLT3 kinase are synergistically sensitive to FLT3 and Hsp90 inhibitors: the key role of the STAT5 signal transduction pathway." Leukemia 19:1605-1612.

ABT-199 (Venetoclax) product description. (2014). https:www.chemietek.com/abt-199--venetoclax-details.aspx. 2 pages.

Chen, G. et al., (Dec. 2012). "Combination of crenolanib with sorafenib produces synergistic pro-apoptotic effects in FLT3-ITD-inhibitor-resistant acute myelogenous leukemias with FLT3 mutations." Abstract from the 54th American Society for Haematology Annual Meeting, Dec. 8-11, 2012. 2 pages.

Pan, R. et al., (2014). "Selective BCL-2 inhibition by ABT-199 causes on target cell death in acute myeloid leukemia." *Cancer Discov.* 4(3):362-375.

Richardson, P. et al., (2018). "Ibrutinib alone or with dexamethasone for relapsed or relapsed and refractory multiple myeloma: phase 2 trial results." *Brit. J. Haematol.* 152:367-379.

(56) References Cited

OTHER PUBLICATIONS

Samlowski, W. (Nov. 2011). Abstract A96: "Phase I study of HSP90 inhibitor MPC-3100 in subjects with refractory or recurrent cancer." *Mol. Cancer Therapeut.* 10 (11 Suppl.). 2 pages.

Sidera, K. et al., (2014). "HSP90 inhibitors: current development and potential in cancer therapy." *Rec. Patents Anti-Cancer Drug Discov.* 9:1-20.

\* cited by examiner

METHODS FOR TREATING CANCER USING HSP90 INHIBITORS

FIELD OF THE INVENTION

The invention relates to the use of HSP90 inhibitors to modulate the immune system for the treatment of cancer and to their use in combination with inhibitors of BCL-2 for treating cancer.

BACKGROUND OF THE INVENTION

Approaches to harness the immune system to effectively identify and subsequently eradicate tumor cells were discovered more than a decade ago. It is only through the recent generation of checkpoint antibodies, notably those that target the programmed cell death protein (PD-1)/programmed death-ligand 1 (PD-L1), has the potential been translated into clinical success. PD-1 is a cell surface inhibitory molecule that is expressed on activated B cells, T cells and myeloid cells. In 1999, B7-H1 (PD-L1) protein was discovered (Dong et al., 1999) and was shown to inhibit T cell responses in vitro (Dong et al., 2002). Subsequent studies showed that PD-L1 is the ligand for PD-1 and the PD-1/PD-L1 interaction is a critical mediator of suppressing T cell responses (Freeman et al., 2000). Thus, the use of therapeutic antibodies to either PD-1 or PD-L1 restores T cell responses (Francisco et al., 2009) and results in improved clinical outcomes (Brahmer et al., 2010).

Activated T cells secrete interferon-γ as part of their immuno-modulatory function, but tumor cells can often coopt the interferon response by up-regulating PD-L1 and increasing cell surface expression (Dong et al., 2002). Increased expression of PD-L1 binds to PD-1 on T cells and suppresses their anti-tumor (cytolytic) function. Notably, monoclonal antibodies that target either PD-1 or PD-L1, which effectively disrupt the PD-1/PD-L1 interaction, have been approved by the Food and Drug Administration (FDA) for a number of indications. However, no small molecule inhibitors that also impinge on this interaction have been approved.

Heat shock proteins (HSPs) are a class of chaperone proteins that are involved in diverse cellular processes such as elevation in temperature, external stresses, and nutrient deprivation. Their basic role as chaperone proteins is to stabilize proteins under such stresses but also to facilitate the correct folding of client proteins. There are several members of proteins within HSPs including HSP27, HSP70 and HSP90. HSP90 is one of the most abundant family members within cells and is prominently involved in cancer due to its client proteins which include various oncogenes including BCR-ABL, BRAF, FLT3, JAK2 and others (Shrestha et al., 2016). Indeed, HSP90 inhibitors have been used in many pre-clinical studies to demonstrate how tumor cells are critically dependent on aberrant pro-survival pathways and how their use results in inhibition of tumor growth. In this pre-clinical setting, HSP90 inhibitors have shown activity in a variety of cancers including breast, colorectal, gastrointestinal, leukemia, lymphomas, melanoma, multiple myeloma, ovarian, pancreatic, prostate and renal.

HSP90 inhibitors have been tested in pre-clinical and early clinical studies relating to various cancers including breast, colorectal, gastro-intestinal, leukemia, lymphomas, melanoma, multiple myeloma, ovarian, pancreatic, prostate and renal. At least 18 HSP90 inhibitors have been investigated in clinical trials, including BIIB021, IPI-493, MPC-3100, Debio0932, DS-2248, HSP990, XL888, SNX5422, TAS-116, BIIB028, IPI-504, KW-2478, alvespimycin, tanespimycin, AT-13387, AUY922, PU-H71 and ganetespib. See reviews by Bhat et al., J. Med. Chem 2014 57:8718-8728; Neckers and Workman Clin. Cancer Res. 2012, 18, 64.

Due to the different chemical properties of each drug and how they were formulated (oral or intravenous), there is no set dosage or schedule for administration. However, the common paradigm applied to other therapeutics such as chemotherapies, or targeted agents, is that each drug is tested in phase 1 trials at increasing doses (dose-escalation) to establish safety and eventually determine the maximum tolerated dose, thus identifying the recommended phase 2 dose (RP2D). Once reached, the drug is then tested in phase 2 trials at the identified RP2D on a larger cohort of patients to determine whether the drug is efficacious.

Whether HSP90 inhibitors can be effective at a lower dose, relative to the established RP2D, has not been addressed. Despite having been tried in various phase 1, 2 and 3 clinical trials, no HSP90 inhibitor has been approved for clinical use. Given the number of client proteins dependent on HSP90 and the number of cellular process these proteins regulate, the question of toxicity remains a possibility. Thus, the clinical doses used, while having the propensity to directly affect tumor cells, may also negatively impact the immune system. This in turn may mitigate any immune-mediated anti-tumor activity. Efforts to reduce the dose of HSP90 inhibitors that may negatively impact the immune system while using sufficient dose to retain HSP90 anti-tumor activity should be explored and forms the basis of this application.

Emerging evidence suggests that HSP90 may also affect tumor immunity. Some non-clinical studies have suggested that high HSP90 inhibitor doses may inhibit various components of the immune system that may be important for tumor clearance (Bae et al., J. Immunol. 2007 178:7730; Bae et al., J. Immunol. 2013 190:1360; Tukaj et al., J. Inflammation 2014 11:10). In addition, many tumor cells express the checkpoint inhibitor protein death ligand 1 (PD-L1) on their surface, which can suppress local cytotoxic T cell activity. For example, PD-L1 expression is found on patient AML cells, increases with disease progression and during relapse (Salih et al., Exp. Hematol. 2006 34:888; Chen et al., Cancer Biol. Ther. 2008 7:622; Berthon et al., Cancer Immunol. Immunother 2010 59:1839) and is associated with poorer overall survival (Brodska et al., Blood 2016 128: 5229). PD-L1 cell surface expression on AML tumor cells may be induced by IFN-γ which is known to be expressed in the immunologically active tumor microenvironment (Berthon et al, Cancer Immunol. Immunother 2010 59:1839; Kronig et al., Eur. J. Hematol. 2013 92:195).

There is a continuing need for improved treatments and drug combinations for treating cancer, including the treatment of cancers that are refractory to current therapies, or those that have relapsed after treatment. The present invention addresses this need with the use of HSP90 inhibitors, and in particular in their combination with inhibitors of the BCL-2 pathway.

SUMMARY OF THE INVENTION

The disclosure provides compositions and methods related to the use of an HSP90 inhibitor for treating cancer in a subject, preferably a human subject, in need of such treatment. The methods relate generally to the use of low dose HSP90 inhibitors in pharmaceutical compositions for the treatment of cancer, either alone, or in combination with other therapies and/or active agents. The methods further relate generally to the use of HSP90 inhibitors in combination with BCL-2 pathway inhibitors. As described in more detail infra, the compositions and methods described here are based, in part, on the discovery that HSP90 inhibitors are effective inhibitors of the interferon-γ (IFN-γ) signal transduction pathway that is activated in diverse types of cancer cells as a mechanism to evade the immune response. This previously unreported immunomodulatory activity of HSP90 occurs at relatively low, non-cytotoxic doses. In addition, the compositions and methods described here are based, in part, on the discovery of synergistic activity between HSP90 inhibitors and BCL-2 pathway inhibitors in cancer.

The disclosure provides methods for treating cancer in a subject in need thereof, the methods comprising administering to the subject an amount of an HSP90 inhibitor and a BCL-2 pathway inhibitor, optionally wherein the amount of the HSP90 inhibitor is a sub-therapeutic amount. The disclosure also provides related pharmaceutical compositions for use in treating cancer, including a pharmaceutical composition comprising an amount of an HSP90 inhibitor and a BCL-2 pathway inhibitor, and a pharmaceutically acceptable carrier or excipient, for treating cancer in a subject in need thereof, optionally wherein the amount of the HSP90 inhibitor is a sub-therapeutic amount; and a pharmaceutical composition comprising an amount of an HSP90 inhibitor for use in combination with a second pharmaceutical composition comprising a BCL-2 pathway inhibitor, for treating cancer in a subject in need thereof, optionally wherein the amount of the HSP90 inhibitor is a sub-therapeutic amount.

In embodiments, the disclosure also provides methods for treating cancer in a subject in need thereof, the method comprising determining BCL-2 expression in a biological sample of the cancer and administering an amount of an HSP90 inhibitor and a BCL-2 pathway inhibitor to the subject having a cancer characterized as positive for BCL-2 expression based on the expression of BCL-2 in the biological sample of the cancer, optionally wherein the HSP90 inhibitor and the BCL-2 pathway inhibitor are administered in the same dosage form or in a different dosage form, optionally wherein the amount of the HSP90 inhibitor is a sub-therapeutic amount.

In accordance with the foregoing methods and uses, the cancer may be further characterized as positive for BCL-2 expression based on the expression of BCL-2 in a biological sample of the cancer. In embodiments, the cancer characterized as positive for BCL-2 expression is a cancer in which a biological sample from the cancer expresses BCL-2 at a level that is at least two-fold higher compared to the BCL-2 expression in a reference sample, for example a sample of non-cancerous cells or tissue. In accordance with the foregoing methods, the BCL-2 expression may be protein expression or gene expression.

In accordance with embodiments of the foregoing methods and uses, the sub-therapeutic amount of the HSP90 inhibitor is less than 90%, less than 75%, less than 50%, or less than 25% of the recommended phase 2 dose of the HSP90 inhibitor.

In accordance with embodiments of the foregoing methods and uses, the cancer is a hematopoietic or lymphoid cancer selected from a leukemia, a lymphoma, and a myeloma. In embodiments, the cancer is a leukemia selected from acute lymphoblastic leukemia (ALL), acute myelogenous leukemia (AML), chronic lymphocytic leukemia (CLL), chronic myelogenous leukemia (CML), and acute monocytic leukemia. In embodiments, the cancer is AML. In embodiments, the cancer is a lymphoma selected from a Hodgkins and a Non-Hodgkin's lymphoma. In embodiments, the cancer is a Non-Hodgkin's B cell lymphoma, preferably selected from a diffuse large B cell lymphoma (DLBCL), Burkitt lymphoma, lymphoblastic lymphoma, and mantle cell lymphoma, and most preferably selected from a diffuse large B cell lymphoma (DLBCL) and a mantle cell lymphoma. In embodiments, the cancer is a myeloma.

In accordance with embodiments of the foregoing methods and uses, the HSP90 inhibitor is selected from a purine-like inhibitor, a resorcinol derivative, a geldanamycin derivative, a pyrazolopyridine derivative, a dihydroindazolone derivative, and a tropane derivative. In embodiments, the HSP90 inhibitor is selected from MPC-0767, AT-13387, tanespimycin, TAS-116, SNX-5422, and XL-888, and pharmaceutically acceptable salts thereof. In embodiments, the HSP90 inhibitor is MPC-0767 or tanespimycin, and pharmaceutically acceptable salts thereof. In embodiments, the HSP90 inhibitor is selected from the group consisting of HSP-990, CNF-2024, PF0498473, tanespimycin, STA-9090, MPC-3100, CUDC-305, XL-888, TAS-116, and pharmaceutically acceptable salts thereof. In embodiments, the HSP90 inhibitor is selected from the group consisting of tanespimycin, alvespimycin, IPI-504, AUY922, AT-13387, ganetespib, KW-2478, CNF2024, MPC3100, BIIB028, SNX5422, PU-H71, MPC-0767, and pharmaceutically acceptable salts thereof.

In accordance with embodiments of the foregoing methods and uses, the BCL-2 pathway inhibitor is selected from ABT-737, AT-101 (Gossypol), APG-1252, A1155463, A1210477, navitoclax, obatoclax, sabutoclax, venetoclax, S 55746, WEHI-539, AMG-176, MIK665, and S641315. In embodiments, the BCL-2 pathway inhibitor is an inhibitor of BCL2, BCLXL, or MCL1. In embodiments, the BCL-2 pathway inhibitor is selected from AMG-176, MIK665 and S641315. In embodiments, the BCL-2 pathway inhibitor is selected from ABT-737, navitoclax, and venetoclax. In embodiments, the BCL-2 pathway inhibitor is venetoclax.

The disclosure also provides methods for treating a BCL-2 expressing hematopoietic or lymphoid cancer in a subject in need thereof, the methods comprising administering to the subject an amount of an HSP90 inhibitor and a BCL-2 pathway inhibitor. In embodiments, the BCL-2 pathway inhibitor is selected from ABT-737, AT-101 (Gossypol), APG-1252, A1155463, A1210477, navitoclax, obatoclax, sabutoclax, venetoclax, S 55746, WEHI-539, AMG-176, MIK665, and 5641315. In embodiments, the BCL-2 pathway inhibitor is venetoclax. In embodiments, the HSP90 inhibitor is selected from a purine-like inhibitor, a resorcinol derivative, a geldanamycin derivative, a pyrazolopyridine derivative, a dihydroindazolone derivative, and a tropane derivative. In embodiments, the HSP90 inhibitor is selected from MPC-0767, AT-13387, tanespimycin, TAS-116, SNX-5422, and XL-888. In embodiments, the HSP90 inhibitor is MPC-0767 or tanespimycin.

In further embodiments of the methods for treating a BCL-2 expressing hematopoietic or lymphoid cancer, the amount of the HSP90 inhibitor is a sub-therapeutic amount.

In further embodiments of the methods for treating a BCL-2 expressing hematopoietic or lymphoid cancer, the cancer is a hematopoietic or lymphoid cancer selected from a leukemia, a lymphoma, and a myeloma. In embodiments, the cancer is a leukemia selected from acute lymphoblastic leukemia (ALL), acute myelogenous leukemia (AML), chronic lymphocytic leukemia (CLL), chronic myelogenous leukemia (CML), and acute monocytic leukemia. In embodiments, the cancer is AML. In embodiments, the cancer is a lymphoma selected from a Hodgkins and a Non-Hodgkin's lymphoma. In embodiments, the cancer is a Non-Hodgkin's B cell lymphoma, preferably selected from a diffuse large B cell lymphoma (DLBCL), Burkitt lymphoma, lymphoblastic lymphoma, and mantle cell lymphoma, and most preferably selected from a diffuse large B cell lymphoma (DLBCL) and a mantle cell lymphoma. In embodiments, the cancer is a myeloma.

In further embodiments of the methods for treating a BCL-2 expressing hematopoietic or lymphoid cancer, the methods comprise determining the amount of BCL-2 expressed in a biological sample of the cancer.

In accordance with any of the foregoing methods and uses, the subject may be human.

In further embodiments, the disclosure provides a pharmaceutical composition comprising an HSP90 inhibitor, and a pharmaceutically acceptable carrier or excipient, for use in treating cancer in a subject in need thereof, wherein the composition comprises an amount of the HSP90 inhibitor that is less than 75% of the recommended phase 2 dose of the HSP90 inhibitor.

In embodiments, the disclosure provides a method for treating cancer in a subject in need thereof, comprising administering to the subject a pharmaceutical composition comprising an amount of an HSP90 inhibitor, and a pharmaceutically acceptable carrier or excipient, wherein the amount of the HSP90 inhibitor is less than 90% or less than 75% of the recommended phase 2 dose of the HSP90 inhibitor. In embodiments, the therapeutically effective amount of an HSP90 inhibitor is the amount effective to inhibit IFN-γ signaling in cancer cells of the subject.

In embodiments of the compositions and methods described here, the amount of the HSP90 inhibitor is less than 50% or less than 25% of the recommended phase 2 dose of the HSP90 inhibitor. In embodiments, the HSP90 inhibitor is selected from the group consisting of HSP-990, CNF-2024, PF0498473, tanespimycin, STA-9090, MPC-3100, CUDC-305, XL-888, TAS-116, and pharmaceutically acceptable salts thereof. In embodiments, the HSP90 inhibitor is selected from the group consisting of tanespimycin, alvespimycin, IPI-504, AUY922, AT13387, ganetespib, KW-2478, CNF2024, MPC3100, BIIB028, SNX5422, PU-H71, MPC-0767, and pharmaceutically acceptable salts thereof.

In embodiments of the compositions and methods described here, the pharmaceutical composition comprises a second active pharmaceutical ingredient (API). In embodiments, second API is selected from an HDAC inhibitor, an ImiD, an anti-VEGFR antibody, a DNA methylation inhibitor, a steroid hormone (ant)agonist, a metabolic enzyme inhibitor, a proteasome inhibitor, an anti-CD20 antibody, an adenosine receptor 2A antagonist, a toll-receptor (ant(agonist), and an immunostimulatory cytokine. In embodiments, second API is selected from cisplatin, docetaxel, gemcitabine, carboplatin, paclitaxel, pemetrexed, etoposide, epirubicin, doxorubicin, cyclophosphamide, ddAC, everolimus, panobinostat, exemestane, letrozole, decitabine, esartinib, abemacicib, merestinib, gefitinib, mocetinostat, azacytidine, etinostat, motolimod, ibrutinib, lenalidomide, idelalisib, enzalutamide, olaparib, prednisone, dexamethasone, vinflunine, vorinostat, galunisertib, bendamustine, oxaliplatin, leucovorin, guadecitabine, dabrafenib, trametinib, vemurafenib, dacarbazine, apatinib, pomalidomide, carfilzomib, sorafenib, 5-fluorouracil, CB-839, CB-1158, GDC-0919, LXH254, AZD4635, AZD9150, PLX3397, LCL161, PBF-509, bevacizumab, Sym004, ramucirumab, ipilimumab, trastuzumab, tremelimumab, obinutuzumab, B-701, utomilumab, rituximab, bevacizumab, interleukin 2, NKTR-214, denenicokin, PEGInterferon 2A, RO7009789, MEDI9447, MK-1248, LY2510924, ARRY-382, MEDI0562, LAG525; NIS793, Lirilumab, varlilumab, GWN323; JTX-2011; Galunisertib; TSR-022; BMS-986016, ramucirumab, urelumab, BMS-986016, REGN3767.

In embodiments of the compositions and methods described here, the second API in the composition is selected from the group consisting of a protein kinase inhibitor, a PD-1/PDL-1 inhibitor, a checkpoint inhibitor, a platinum based anti-neoplastic agent, a topoisomerase inhibitor, a nucleoside metabolic inhibitor, an alkylating agent, an intercalating agent, a tubulin binding agent, an inhibitor of DNA repair, and combinations thereof. In embodiments, the second API in the composition is a PD-1/PD-L1 inhibitor. In embodiments, the PD-1/PD-L1 inhibitor is selected from the group consisting of nivolumab, pembrolizumab, AMP-514/MEDI-0680, atezolizumab, durvalumab, avelumab, BMS936559, AMP-224, BGB-A317, SHR-1210, and JTX-4014. In embodiments, the amount the PD-1/PD-L1 inhibitor is less than 75% of the recommended phase 2 dose of the PD-1/PD-L1 inhibitor.

In embodiments of the compositions and methods described here, the second API in the composition is a CTLA-4 inhibitor. In embodiments, the CTLA-4 inhibitor is selected from tremlimumab and ipilimumab. In embodiments, the second API in the composition is a checkpoint inhibitor. In embodiments, the checkpoint inhibitor is selected from the group consisting of an anti-CD27 antibody, an anti-B7-H3 antibody, an anti-KIR antibody, an anti-LAG-3 antibody, an anti-TIM3 antibody, an anti-OX40 antibody, an anti-4-1BB/CD137 antibody, an anti-CD40 antibody, an anti-TRX518 antibody, an anti-CD73 antibody, and an anti-GITR antibody. In embodiments, the checkpoint inhibitor is selected from the group consisting of varlilumab, MGA217, lirilumab, BMS-986016, urelumab, MEDI-0562, SEA-CD40, TRX518, and MK-4166. In embodiments, the second API in the composition is a DNA repair inhibitor selected from the group consisting of olaparib, rucaparib, niraparib, talazoparib veliparib, CEP-9722, and CEP-8983.

In embodiments of the compositions and methods described here, the cancer is selected from the group consisting of brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, a T-cell lymphoma, non-Hodgkin's lymphoma, mantle cell lymphoma, multiple myeloma, B-cell lymphoma, leukemia, and Hodgkin's lymphoma. In embodiments, the cancer is selected from the group consisting of melanoma, Hodgkin's lymphoma, non-small cell lung cancer, bladder cancer, non-Hodgkin's lymphoma, leukemia, T-cell lymphoma, and renal cell carcinoma.

In embodiments of the compositions and methods described here, the cancer is selected from a cancer that has shown clinical sensitivity to PD-1/PD-L1 therapies, or a cancer that is utilizing the PD-1/PD-L1 pathway to evade the host immune system. In embodiments, the cancer is selected from the group consisting of melanoma, Hodgkin's lymphoma, non-small cell lung cancer, bladder cancer, non-Hodgkin's lymphoma, leukemia, T-cell lymphoma, and renal cell carcinoma.

In embodiments of the compositions and methods described here, the pharmaceutical composition comprises an amount of an HSP90 inhibitor effective to inhibit interferon-γ signal transduction in cancer cells of the subject.

In embodiments, the subject is human.

In embodiments, the pharmaceutical composition is adapted for oral or buccal administration. In embodiments, the pharmaceutical composition is adapted for parenteral administration.

DETAILED DESCRIPTION

Figure 1A:
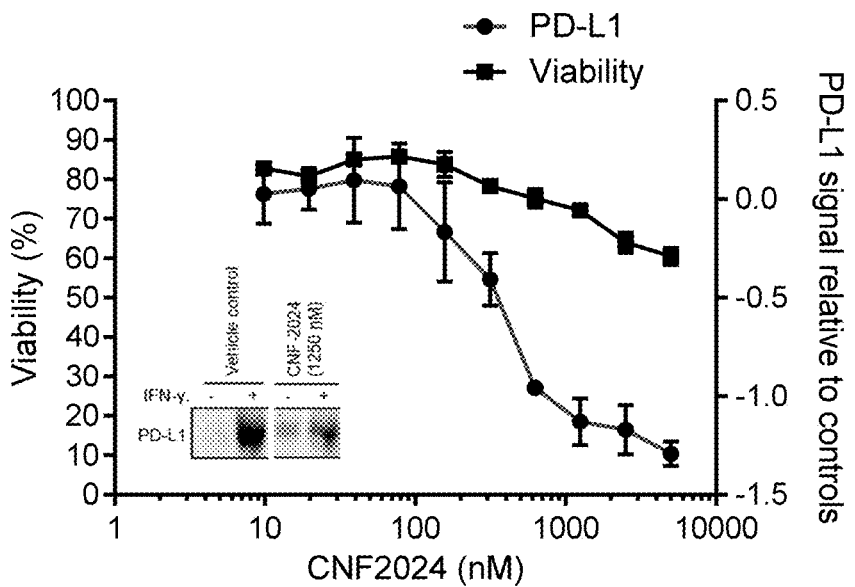
FIG. 1A-D. Validation dose response curves of HSP90 inhibitors tested in the original screen. A) CNF2024; B) PF04928473; C) tanespimycin; D) HSP-990. SK-MEL-28 cells treated with IFN-γ and with the indicated HSP90 inhibitor at different concentrations. Cells were assayed for cell viability (square, % viability on left axis) and PD-L1 expression (circle, Z-score right axis) at 48 h after treatment of IFN-γ and/or HSP90 inhibitors. Quadruplicate wells were used for determination of cell viability and PD-L1 expression. Average values were plotted. The inset shows western blot data from SK-MEL-28 cells treated with vehicle, vehicle+IFN-γ, indicated HSP90 inhibitor alone, or IFN-γ+ indicated HSP90 inhibitor. Lysates were probed with anti PD-L1 antibody.
Figure 1B:
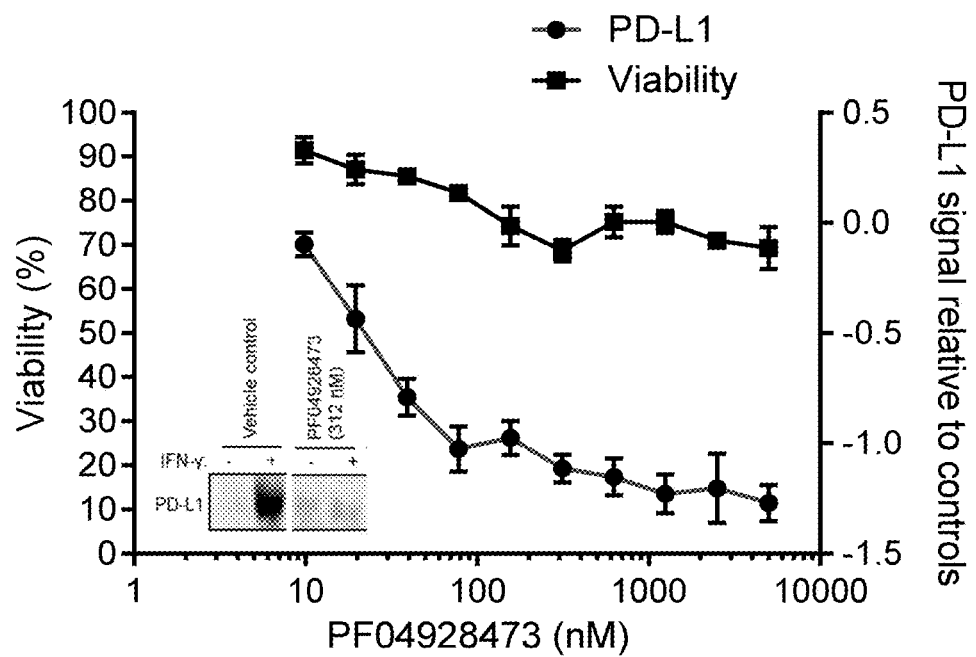
Figure 1C:
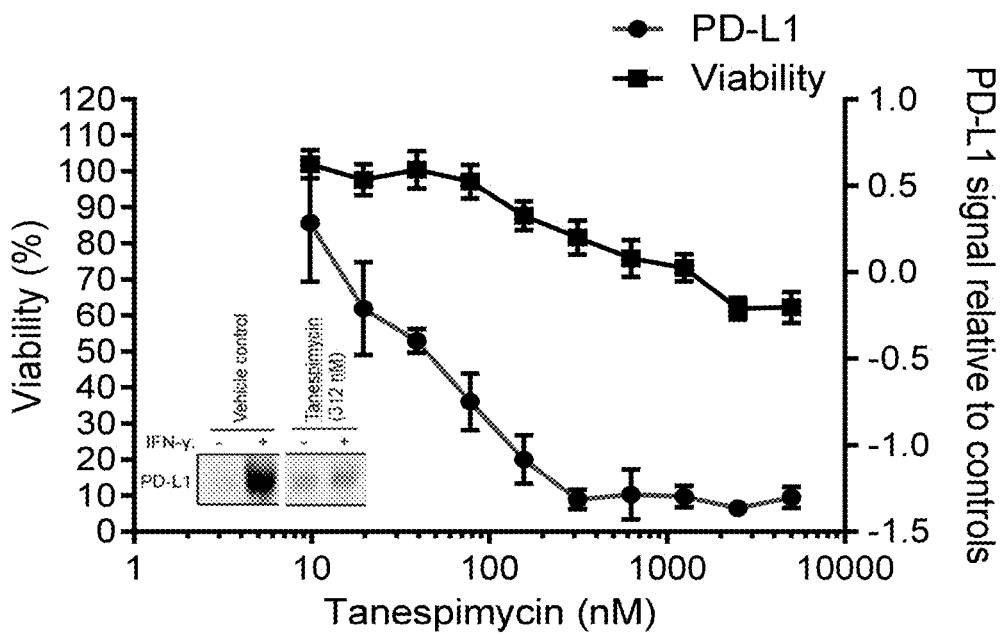
Figure 1D:
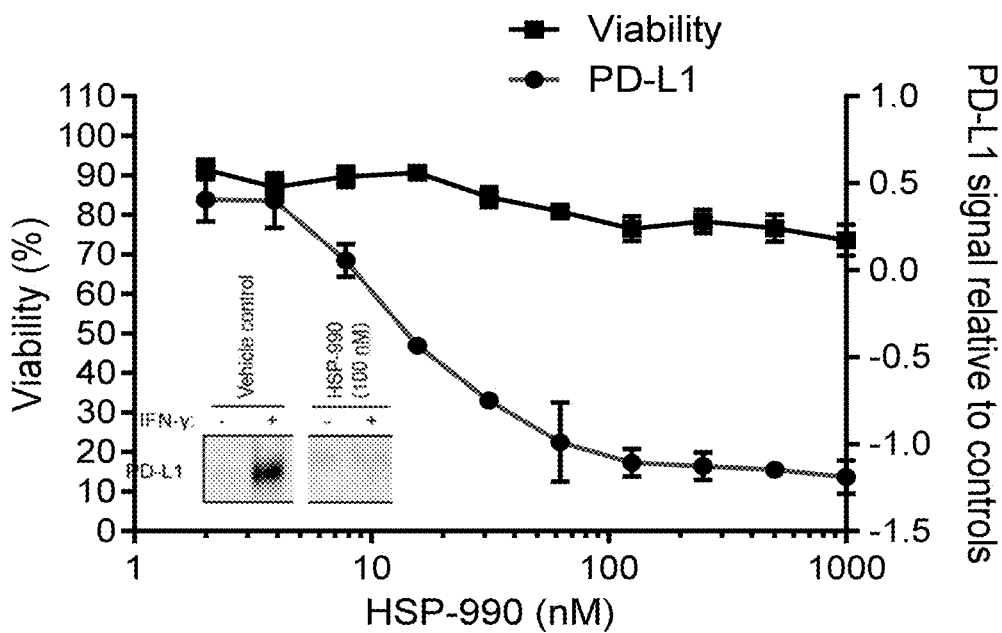
Figure 2A:
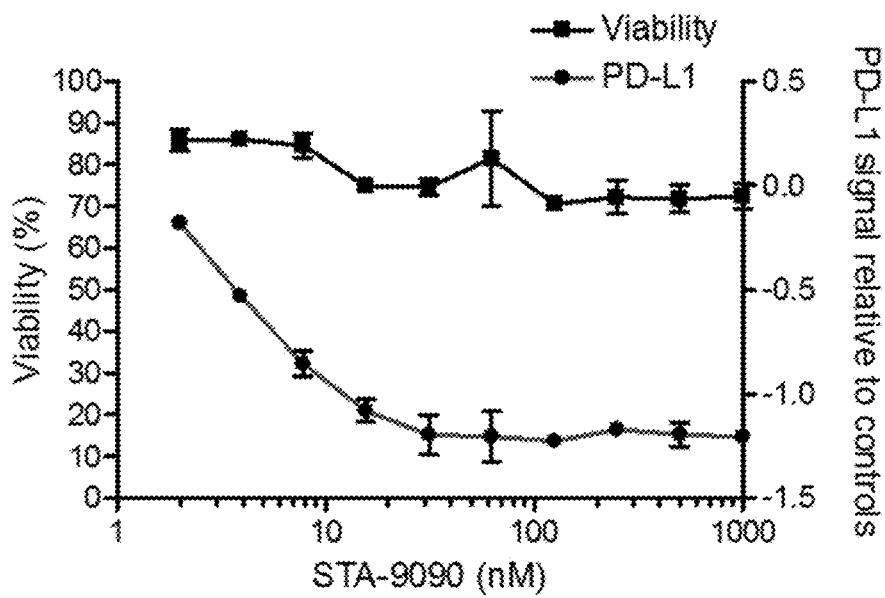
FIG. 2A-E. Dose response curves of 5 additional HSP90 inhibitors. A) STA-9090, B) CUDC-305, C) MPC-3100, D) XL-888 and E) TAS-116. SK-MEL-28 cells treated with IFN-γ (50 ng/ml) and with the indicated HSP90 inhibitor at different concentrations. Cells were assayed for cell viability (square, % viability on left axis) and PD-L1 expression (circle, Z-score right axis) at 48 h after treatment of IFN-γ and/or HSP inhibitors. Quadruplicate wells were used for determination of cell viability and PD-L1 expression. Average values were plotted.
Figure 2B:
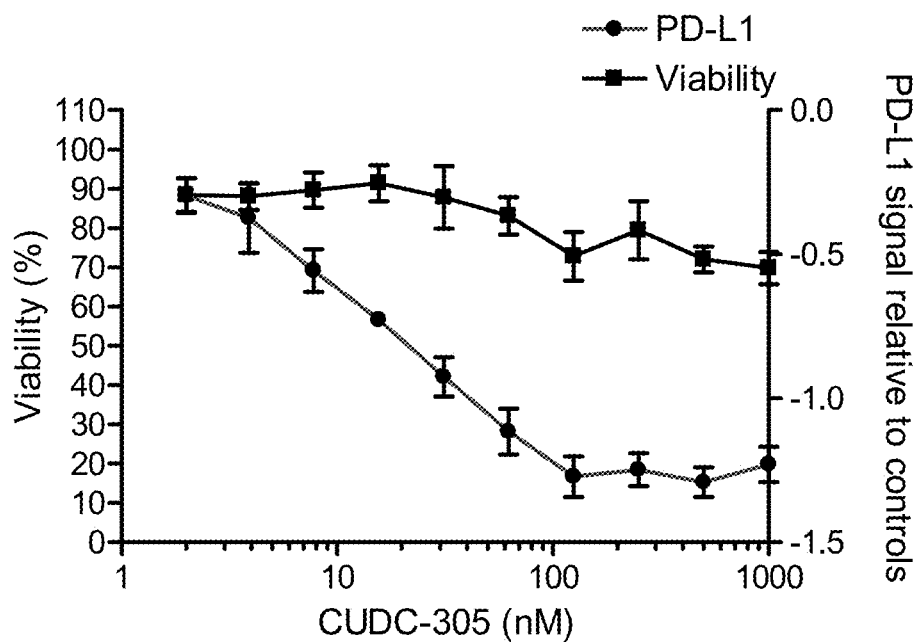
Figure 2C:
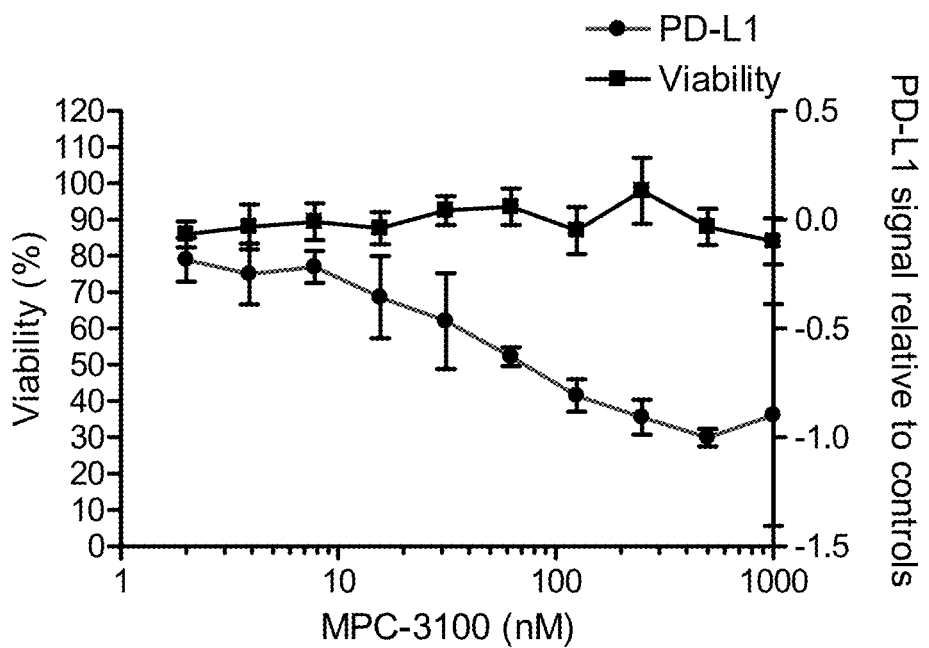
Figure 2D:
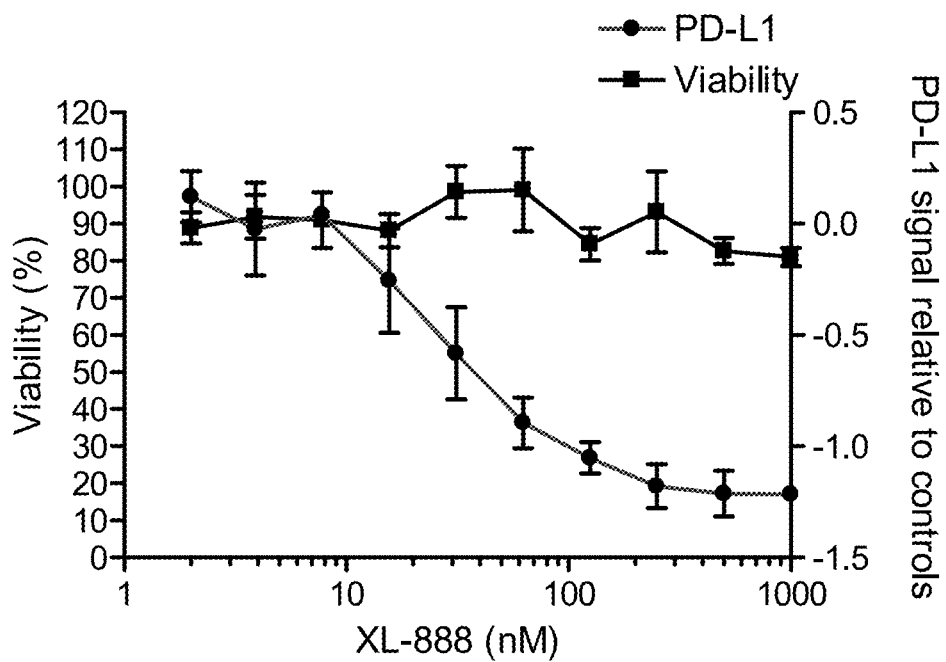
Figure 2E:
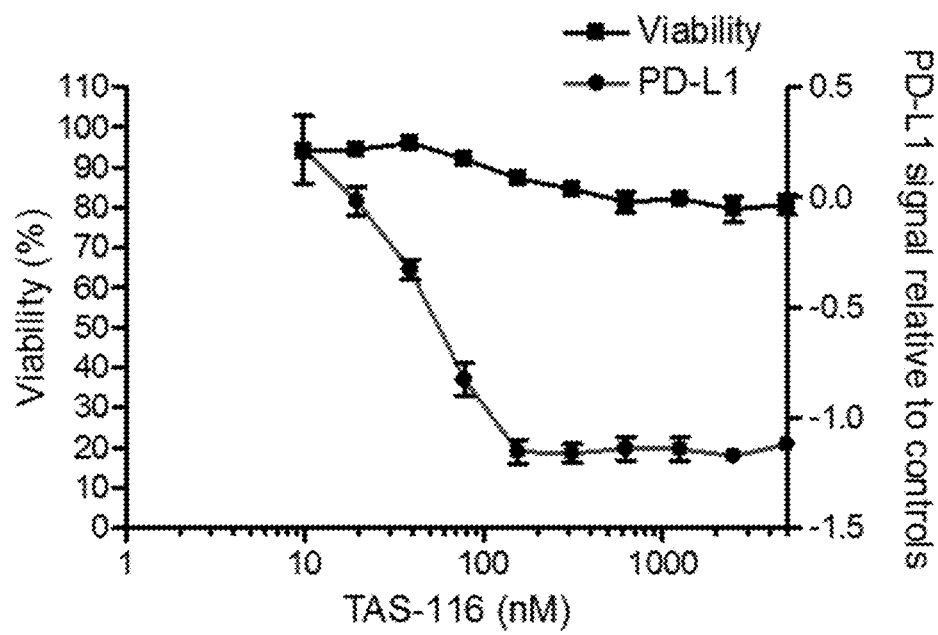

Leveraging the immune system has proven to have clinical efficacy in a number of cancers. By disengaging the inhibitory interaction of PD-1/PD-L1 between T cells and tumor cells, checkpoint antibody therapies have changed the paradigm for how a number of cancers are treated. In embodiments, the disclosure provides compositions and methods for treating or preventing cancer in a subject in need thereof, where the cancer is utilizing the PD-1/PD-L1 pathway to evade the host immune system. The methods comprise administering to the subject an effective amount of a HSP90 inhibitor, either alone or in combination with a second active pharmaceutical agent (API), such as checkpoint inhibitor. The compositions and methods described here are based, in part, on the discovery that HSP90 inhibitors are effective to block the interferon-γ (IFN-γ) signal transduction response of tumor cells at low, non-cytotoxic doses. Tumor cells utilize IFN-γ signaling to induce PD-L1, a mechanism for evasion of the host immune response. Accordingly, in embodiments, the compositions and methods described here exploit this property of HSP90 inhibitors to provide new treatments and treatment regimens for cancer therapy. In embodiments, provided are compositions and methods related to the use of an HSP90 inhibitor for treating cancer in a subject, preferably a human subject, in need of such treatment. The present disclosure generally relates to the use of HSP90 inhibitors to treat cancers at lower doses than those previously expected to be effective. For example, at doses that are less than 90% of the recommended phase 2 dose ("RP2D") of the HSP90 inhibitor, or less than 75%, or less than 50%, or less than 25% of the recommended phase 2 dose of the HSP90 inhibitor. In the context of the present disclosure, such doses may also be referred to as 'sub-therapeutic' doses of the HSP90 inhibitor because they are below the dose expected from prior phase 2 studies to be therapeutically effective when the HSP90 inhibitor is administered as monotherapy in the treatment of cancer. In embodiments, a 'sub-therapeutic dose' of an HSP90 inhibitor refers to a dose that is in the range of 0-25%, 25-50%, 50-75% or 75-90% of the RP2D for that inhibitor.

In addition, the disclosure provides compositions and methods related to the synergistic anti-cancer activity of HSP90 inhibitors generally with inhibitors of the BCL-2 signaling pathway. As described in more detail below, six different structural classes of HSP90 inhibitors (defined according to molecular scaffold) acted synergistically with the BCL-2 inhibitor venetoclax to inhibit cell viability in haematopoietic and lymphoid cancers. In addition, the level of BCL-2 expression in the cancer cells correlated with the anti-cancer activity of the combination. Accordingly, the disclosure also provides compositions and methods related to combination therapy with HSP90 inhibitors and BCL-2 pathway inhibitors based on the synergistic anti-cancer activity of these agents, including methods of identifying cancers likely to benefit from this combination therapy by assessing the BCL-2 expression of the cancer cells.

HSP90 Inhibitors

In accordance with the methods and compositions described here, the HSP90 inhibitor may be any inhibitor of HSP90, for example, any inhibitor that abrogates the ATPase activity of HSP90. In embodiments, the HSP90 inhibitor is selected from purine-like inhibitors, such as MPC-0767, resorcinol derivatives, such as AT-13387, geldanamycin derivatives, such as tanespimycin, pyrazolopyridine derivatives, such as TAS-116, dihydroindazolone derivatives, such as SNX-5422, and tropane derivatives such as XL-888. Table 1 below shows the chemical structure of a representative of each of these structural classes of HSP90 inhibitors.

Accordingly, in embodiments, the HSP90 inhibitor may be selected from AT-13387, AUY922, BIIB028, CNF-2024, CUDC-305, ganetespib, HSP-990, IPI-504, KW-2478, MPC-0767, MPC-3100, PF0498473, PU-H71, STA-9090, SNX-5422, TAS-116, XL-888, tanespimycin, alvespimycin, and pharmaceutically acceptable salts thereof.

TABLE 1

Representative HSP90 Inhibitors for Each of Six Chemical Classes

| HSP90 Inhibitor | Class | Structure |
|---|---|---|
| MPC-0767 | purine-like | 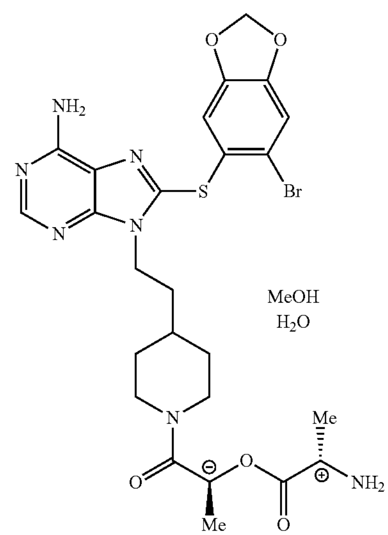 |
| AT-13387 | resorcinol derivatives | 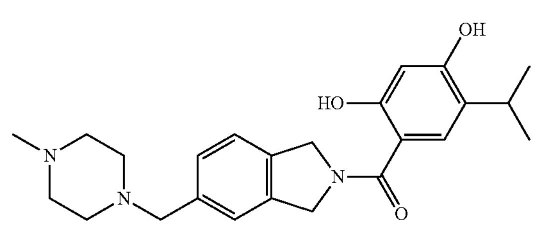 [SMILES: CC(C)c1cc(C(=O)N2Cc3ccc(CN4CCN(C)CC4)cc3C2)c(O)cc1O] |

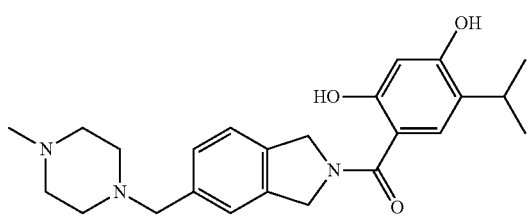

TABLE 1-continued

Representative HSP90 Inhibitors for Each of Six Chemical Classes

| HSP90 Inhibitor | Class | Structure |
| --- | --- | --- |
| tanespimycin | geldanamycin derivatives | 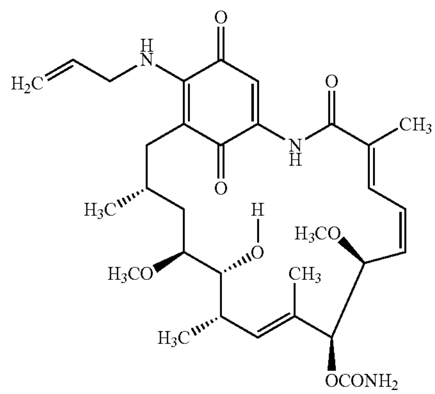 |
| TAS-116 | pyrazolopyridine derivatives | 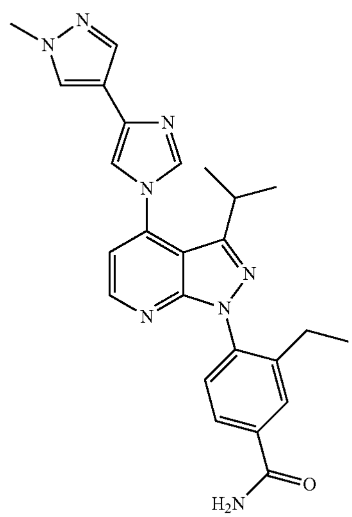 [SMILES: CCc1cc(C(N)=O)ccc1-n1nc(C(C)C)c2c(-n3cnc(-c4cnn(C)c4)c3)ccnc21] |
| SNX-5422 | dihydroindazolone derivatives | 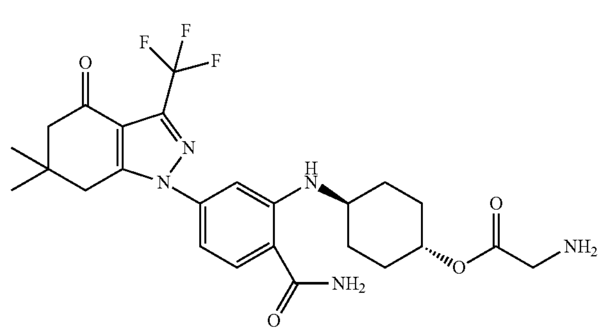 [SMILES: CC1(C)CC(=O)c2c(C(F)(F)F)nn(-c3ccc(C(N)=O)c(N[C@H]4CC[C@H](OC(=O)CN)CC4)c3)c2C1] |

TABLE 1-continued

Representative HSP90 Inhibitors for Each of Six Chemical Classes

| HSP90 Inhibitor | Class | Structure |
|---|---|---|
| XL-888 | tropane derivatives | 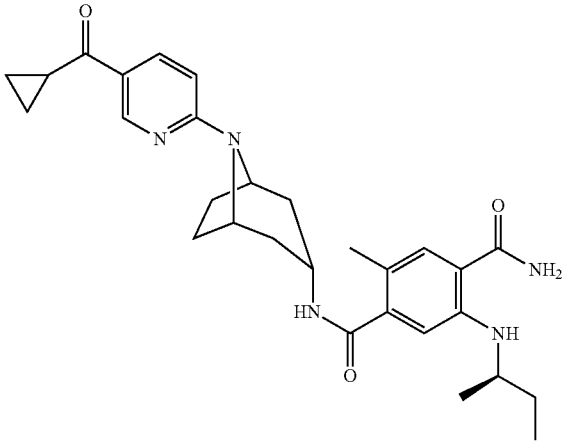 [SMILES: CC[C@@H](C)Nc1cc(C(=O)NC2CC3CCC(C2)N3c2ccc(C(=O)C3CC3)cn2)c(C)cc1C(N)=O] |

Methods

The present disclosure provides unique therapeutic approaches to cancer treatment based upon combination therapy utilizing an HSP90 inhibitor and a BCL-2 pathway inhibitor. The compositions and methods relating to combination therapy with HSP90 inhibitors and BCL-2 pathway inhibitors described here exploit the synergistic anti-cancer activity of these two classes of therapeutic agents, as described herein. Related methods of identifying a patient for targeted therapy with a combination of an HSP90 inhibitor and a BCL-2 pathway inhibitor are also provided. In embodiments, the methods comprise measuring, determining, or assaying the expression of BCL-2 in a cancer biopsy or biological sample or the cancer from the patient. The BCL-2 expression may be protein expression or gene expression and may, measured according to routine methods known in the art. For example, gene expression may be measured by methods comprising a quantitative reverse transcription polymerase chain reaction (RT-PCR). BCL-2 protein expression may be measured by methods including, for example, antibody-based detection methods such as those comprising immunohistochemistry, immunocytochemistry, enzyme linked immunosorbent assay (ELISA), and flow cytometry.

The disclosure also provides methods of treating cancer with a "low dose" or "sub-therapeutic dose" of an HSP90 inhibitor based upon the inventors' discovery that such amounts of HSP90 inhibitors are effective to inhibit the INFγ signaling pathway utilized by diverse types of cancers to evade the host immune response. Accordingly, in embodiments, a cancer treated by the "low dose" or "sub-therapeutic dose" of an HSP90 inhibitor according to the methods described here is characterized by its utilization of the PD-1/PD-L1 pathway to evade the host immune system. Non-limiting examples of such cancers include melanoma, Hodgkin's lymphoma, non-small cell lung cancer, bladder cancer, non-Hodgkin's lymphoma, leukemia, T-cell lymphoma, and renal cell carcinoma.

In addition, the present disclosure provides unique therapeutic approaches to cancer treatment based upon combination therapy utilizing a "low dose" or "sub-therapeutic dose" of an HSP90 inhibitor and at least one additional therapeutic agent. In embodiments, the combination therapies described herein exploit the unique immunomodulatory activity of HSP90 inhibitors described here, which is achieved at a sub-therapeutic dose of the HSP90 inhibitor, and which is expected to provide a synergistic effect when combined with other therapeutic agents in the treatment of cancer.

Both monotherapy and combination therapy methods of treating cancer with HSP90 inhibitors are contemplated by the present disclosure. Combination therapies are discussed infra. In the context of monotherapy, in embodiments the HSP90 inhibitor is administered at a "low dose" or "sub-therapeutic dose" which is characterized as an amount of the HSP90 inhibitor that is less than about 75% of the recommended phase 2 dose of the HSP90 inhibitor. The terms "low dose" and "sub-therapeutic dose" are used interchangeably herein in reference to the amount of an HSP90 inhibitor for use in the methods described here.

In embodiments of the methods described here, the subject in need of treatment may be one having a cancer that expresses BCL-2, preferably a cancer that expresses BCL-2 at least two-fold higher than a reference sample comprising non-cancer cells or tissues.

In embodiments of the methods described here, the subject in need of treatment may be one having a cancer that utilizes the PD-1/PD-L1 pathway to evade the host immune system.

In embodiments of the methods described here, the subject in need of treatment may be one having a cancer that is non-responsive or refractory to, or has relapsed after, treatment with a 'standard of care' or first-line therapeutic agent. In this context, the terms "non-responsive" and "refractory" are used interchangeably and refer to the subject's response to therapy as not clinically adequate, for example to stabilize or reduce the size of one or more solid tumors, to slow tumor progression, to prevent, reduce or decrease the incidence of new tumor metastases, or to relieve one or more symptoms associated with the cancer. A cancer that is refractory to a particular drug therapy may also be described as a drug resistant cancer. In a standard therapy for the cancer, refractory cancer includes disease that in progressing despite active treatment while "relapsed" cancer includes cancer that progresses in the absence of any current therapy, but following successful initial therapy. Accordingly, in embodiments, the subject is one who has undergone one or more previous regimens of therapy with one or more 'standard of care' therapeutic agents. In such cases, the subject's cancer may be considered refractory or relapsed.

In accordance with the methods described herein, a "subject" includes a mammal. The mammal can be e.g., any mammal, e.g., a human, primate, mouse, rat, dog, cat, cow, horse, goat, camel, sheep or a pig. Preferably, the subject is a human. The term "patient" refers to a human subject.

In embodiments, the cancer treated according to the methods described here is selected from the group consisting of brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, a T-cell lymphoma, non-Hodgkin's lymphoma, mantle cell lymphoma, multiple myeloma, B-cell lymphoma, leukemia, and Hodgkin's lymphoma.

In embodiments, the cancer is selected from a cancer that expresses BCL-2, preferably one the expresses BCL-2 at least two-fold higher compared to a reference non-cancerous tissue.

In embodiments, the cancer is a hematopoietic or lymphoid cancer selected from a leukemia, a lymphoma, and a myeloma. In embodiments, the cancer is a leukemia selected from acute lymphoblastic leukemia (ALL), acute myelogenous leukemia (AML), chronic lymphocytic leukemia (CLL), chronic myelogenous leukemia (CML), and acute monocytic leukemia. In embodiments, the cancer is AML. In embodiments, the cancer is a lymphoma selected from a Hodgkins and a Non-Hodgkin's lymphoma. In embodiments, the cancer is a Non-Hodgkin's B cell lymphoma, preferably selected from a diffuse large B cell lymphoma (DLBCL), Burkitt lymphoma, lymphoblastic lymphoma, and mantle cell lymphoma, and most preferably selected from a diffuse large B cell lymphoma (DLBCL) and a mantle cell lymphoma. In embodiments, the cancer is a myeloma.

As used herein, "combination therapy" or "co-therapy" includes the administration of a therapeutically effective amount of an HSP90 inhibitor as part of a treatment regimen intended to provide the beneficial effect from the co-action of the an HSP90 inhibitor and at least one additional "active pharmaceutical ingredient" ("API"). "Combination therapy" is not intended to encompass the administration of two or more therapeutic compounds as part of separate monotherapy regimens that incidentally and arbitrarily result in a beneficial effect that was not intended or predicted.

Preferably, the administration of a composition comprising an HSP90 inhibitor in combination with one or more additional APIs, such as a BCL-2 pathway inhibitor, as discussed herein provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages, for example a low dose of the HSP90 inhibitor as described here, and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

In the context of combination therapy, administration of the HSP90 inhibitor composition may be simultaneous with or sequential to the administration of the one or more additional active agents, such as the BCL-2 pathway inhibitor. In another embodiment, administration of the different components of a combination therapy may be at different frequencies.

The additional API(s) can be formulated for co-administration with the HSP90 inhibitor composition in a single dosage form. The additional API(s) can also be administered separately from the dosage form that comprises the HSP90 inhibitor. When the additional active agent is administered separately from HSP90 inhibitor, it can be by the same or a different route of administration, and/or at the same or different time.

In embodiments, the at least one additional API may be a BCL-2 pathway inhibitor, a protein kinase inhibitor, a PD-1/PD-L1 inhibitor, a checkpoint inhibitor, a platinum based anti-neoplastic agent, a topoisomerase inhibitor, a nucleoside metabolic inhibitor, an alkylating agent, an intercalating agent, a tubulin binding agent, an inhibitor of DNA repair, and combinations thereof. In embodiments, the at least one additional API is a BCL-2 pathway inhibitor or a PD-1/PD-L1 inhibitor. In embodiments, a sub-therapeutic amount of the HSP90 inhibitor is administered with the BCL-2 pathway inhibitor or the PD-1/PD-L1 inhibitor.

In embodiments, the at least one additional API is a PD-1/PD-L1 inhibitor. In embodiments, the PD-1/PD-L1 inhibitor is selected from AMP-224, AMP-514/MEDI-0680, atezolizumab (MPDL3280A), avelumab (MSB0010718C), BGB-A317, BMS936559, cemiplimab (REGN2810), durvalumab (MEDI-4736), JTX-4014, nivolumab (BMS-936558), pembrolizumab (Keytruda, MK-3475), GLS-010, and SHR-1210.

In embodiments, the at least one additional API is a BCL-2 pathway inhibitor. In embodiments, the BCL-2 pathway inhibitor is selected from ABT-737, AT-101 (Gossypol), APG-1252, A1155463, A1210477, navitoclax, obatoclax, sabutoclax, venetoclax, S 55746, and WEHI-539. In embodiments, the BCL-2 pathway inhibitor is an inhibitor of BCL2, BCLXL, or MCL1. In embodiments, the BCL-2 pathway inhibitor is selected from AMG-176, MIK665 and S641315. In embodiments, the BCL-2 pathway inhibitor is selected from ABT-737, navitoclax, and venetoclax. In embodiments, the BCL-2 pathway inhibitor is venetoclax.

In embodiments, the at least one additional API is a CTLA-4 inhibitor. In embodiments, the CTLA-4 inhibitor is selected from tremlimumab and ipilimumab.

In embodiments, the at least one additional API is a check point inhibitor. Treatment with these compounds works by targeting molecules that serve as checks and balances on immune responses. By blocking these inhibitory molecules or, alternatively, activating stimulatory molecules, these treatments are designed to unleash or enhance pre-existing anti-cancer immune responses. In embodiments, the check point inhibitor may be selected from an antibody such as an anti-CD27 antibody, an anti-B7-H3 antibody, an anti-KIR antibody, an anti-LAG-3 antibody, an anti-4-1BB/CD137 antibody, an anti-GITR antibody (e.g., TRX518, MK-4166), pembrolizumab (Keytruda™, a PD-1 antibody), MPDL3280A (a PD-L1 antibody), varlilumab (CDX-1127, an anti-CD27 antibody), MGA217 (an antibody that targets B7-H3), lirilumab (a KIR antibody), BMS-986016 (a LAG-3 antibody), urelumab (a 4-1BB/CD137 antibody), an anti-TIM3 antibody, MEDI-0562 (a OX40 antibody), SEA-CD40 (an anti-CD40 antibody), tremelimumab (anti-CTLA4 antibody), an anti-OX40 antibody, and an anti-CD73 antibody. In embodiments, the checkpoint inhibitor is selected from a small molecule inhibitor of CD73 (as described, for example, in *Cancer Immunol Res* 2016; 4 (11 Suppl): Abstract nr PR10). In embodiments, the checkpoint inhibitor is selected from varlilumab, MGA217, lirilumab, BMS-986016, urelumab, MEDI-0562, SEA-CD40, TRX518, or MK-4166. In embodiments, the at least one additional API is a DNA repair inhibitor. In embodiments, the DNA repair inhibitor is selected from the group consisting of olaparib, rucaparib, niraparib, talazoparib veliparib, CEP-9722, and CEP-8983.

In embodiments, the at least one additional API is a DNA repair inhibitor selected from olaparib, rucaparib, niraparib, talazoparib veliparib, CEP-9722, and CEP-8983.

In embodiments, the at least one additional API is a VEGF inhibitor. In embodiments, the VEGF inhibitor is selected from sunitinib, pazopanib, bevacizumab, sorafenib, cabozantinb, and axitinib.

In embodiments, at least one additional API is selected from ddAC, panobinostat, exemestane, letrozole, esartinib, merestinib, mocetinostat, etinostat, motolimod, ibrutinib, lenalidomide, idelalisib, enzalutamide, prednisone, dexamethasone, vinflunine, vorinostat, galunisertib, bendamustine, oxaliplatin, leucovorin, guadecitabine, trametinib, vemurafenib, dacarbazine, apatinib, pomalidomide, carfilzomib, sorafenib, 5-fluorouracil, CB-839, CB-1158, GDC-0919, LXH254, AZD4635, AZD9150, PLX3397, LCL161, PBF-509, Sym004, trastuzumab, obinutuzumab, B-701, utomilumab, rituximab, NKTR-214, PEGInterferon 2A, RO7009789, MEDI9447, MK-1248, LY2510924, ARRY-382, MEDI0562, LAG525, NIS793, GWN323, JTX-2011, TSR-022, and REGN3767.

In embodiments, the at least one additional API is directed towards targeted therapy, wherein the treatment targets the cancer's specific genes, proteins, or the tissue environment that contributes to cancer growth and survival. This type of treatment blocks the growth and spread of cancer cells while limiting damage to healthy cells. In embodiments, the at least one additional API is directed towards anti-angiogenesis therapy, wherein the treatment focuses on stopping angiogenesis, which is the process of making new blood vessels. Because a tumor needs the nutrients delivered by blood vessels to grow and spread, the goal of anti-angiogenesis therapies is to "starve" the tumor. One anti-angiogenic drug, bevacizumab (Avastin), has been shown to slow tumor growth for people with metastatic renal carcinoma. Bevacizumab combined with interferon slows tumor growth and spread.

In embodiments, the at least one additional API is directed towards immunotherapy, also called biologic therapy, which is designed to boost the body's natural defenses to fight cancer. It uses materials made either by the body or in a laboratory to improve, target, or restore immune system function. For example, interleukin-2 (IL-2) is a drug that has been used to treat kidney cancer as well as AM0010, and interleukin-15. They are cellular hormones called cytokines produced by white blood cells and are important in immune system function, including the destruction of tumor cells. Alpha-interferon is another type of immunotherapy used to treat kidney cancer that has spread. Interferon appears to change the proteins on the surface of cancer cells and slow their growth. Many combination therapies of IL-2 and alpha-interferon for patients with advanced kidney cancer combined with chemotherapy are more effective than IL-2 or interferon alone.

In embodiments, the at least one additional API is a cancer vaccine, designed to elicit an immune response against tumor-specific or tumor-associated antigens, encouraging the immune system to attack cancer cells bearing these antigens. In embodiments, the cancer vaccine is AGS-003, DCVax, NY-ESO-1 or a personalized vaccine derived from patient's cancer cells.

In embodiments, the at least one additional API is an immunostimulant, such as a recombinant protein, used to activate the immune system to attack cancer cells. In embodiments, the immunostimulant is denenicokin (recombinant IL-21).

In embodiments, the at least one additional API is a small molecule that modulates the immune system to encourage the elimination of cancer cells. In embodiments, the small molecule is epacadostat or navoximod (both IDO inhibitors), or PLX3397 (an inhibitor of CSF-1R).

In embodiments, the at least one additional API is selected from taxol, vincristine, doxorubicin, idarubicin, temsirolimus, carboplatin, ofatumumab, rituximab, and combinations thereof.

In embodiments, the at least one additional API is selected from chlorambucil, ifosfamide, doxorubicin, mesalazine, thalidomide, lenalidomide, temsirolimus, everolimus, fludarabine, cytarabine, mitoxantrone, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In embodiments, the at least one additional API may be the patient's own immune cells which have been removed from a patient, genetically modified or treated with chemicals to enhance their activity, and then re-introduced into the patient with the goal of improving the immune system's anti-cancer response.

"Combination therapy" also embraces the administration of HSP90 inhibitors as described herein in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

The non-drug treatment can be selected from chemotherapy, radiation therapy, hormonal therapy, anti-estrogen therapy, gene therapy, surgery (e.g. radical nephrectomy, partial nephrectomy, laparoscopic and robotic surgery), radiofrequency ablation, and cryoablation. For example, a non-drug therapy is the removal of an ovary (e.g., to reduce the level of estrogen in the body), thoracentesis (e.g., to remove fluid from the chest), paracentesis (e.g., to remove fluid from the abdomen), surgery to remove or shrink angiomyolipomas, lung transplantation (and optionally with an antibiotic to prevent infection due to transplantation), or oxygen therapy (e.g., through a nasal cannula containing two small plastic tubes or prongs that are placed in both nostrils, through a face mask that fits over the nose and mouth, or through a small tube inserted into the windpipe through the front of the neck, also called transtracheal oxygen therapy).

In embodiments, the amount of the HSP90 inhibitor is a sub-therapeutic amount and the cancer is selected from a non-small cell lung cancer (NSCLC) and the at least one additional API is selected from cisplatin/docetaxel, bevacizumab, gemcitabine, carboplatin, (nab-) paclitaxel, pemetrexed, etoposide, Sym004 (anti-EGFR), gefitinib, mocetinostat, PLX3397, etinostat, AZD4635 (A2aR antagonist), tremelimumab, ipilimumab, and PBF-509 (A2AR antagonist).

In embodiments, the amount of the HSP90 inhibitor is a sub-therapeutic amount and the cancer is selected from a solid tumor and the at least one additional API is selected from ramucirumab, abemacicib, merestinib, RO7009789 (anti-CD40), MEDI9447 (anti-CD73), MK-1248 (anti-GITR), olaparib, cediranib, 5FU, leucovorin, oxaliplatin, ibrutinib, LY2510924 (CXCR4 antagonist), ARRY-382 (CSFR1i), MEDI0562 (anti-OX40), LAG525 (anti-LAG3), NIS793, lirilumab (anti-KIR), NKTR-214 (selective IL-2); varlilumab (anti-CD27), IL-21 (denenicokin); GWN323 (anti-GITR); JTX-2011 (anti-ICOS), galunisertib; TSR-022 (anti-TIM3); BMS-986016 (anti-LAG3), REGN3767 (anti-LAG3); GDC-0919 (IDO inh), CB-1158 (Arginase inh), and AZD4635 (A2aR antagonist).

In embodiments, the amount of the HSP90 inhibitor is a sub-therapeutic amount and the cancer is selected from mesothelioma, colorectal cancer, urothelial cancer, gastric cancer, and liver cancer and the at least one additional API is selected from tremelimumab and ipilimumab.

In embodiments, the amount of the HSP90 inhibitor is a sub-therapeutic amount and the cancer is selected from breast cancer and the at least one additional API is selected from nab-paclitaxel, epirubicin, doxorubicin, cyclophosphamide, ddAC, everolimus, panobinostat, LCL161 (IAP inh), anti-estrogen therapy (exemestane), letrozole, decitabine, and trastuzumab.

In embodiments, the amount of the HSP90 inhibitor is a sub-therapeutic amount and the cancer is an ALK positive cancer, such as an ALK positive lung cancer, including some forms of NSCLC, and the at least one additional API is selected from esartinib.

In embodiments, the amount of the HSP90 inhibitor is a sub-therapeutic amount and the cancer is a urothelial cancer and the at least one additional API is selected from gemcitabine/carboplatin, docetaxel, paclitaxel, vinflunine, B-701 (anti-FGFR3) and vorinostat.

In embodiments, the amount of the HSP90 inhibitor is a sub-therapeutic amount and the cancer is an ovarian cancer and the at least one additional API is selected from a multi-epitope anti-folate vaccine, motolimod, carboplatin, and paclitaxel.

In embodiments, the amount of the HSP90 inhibitor is a sub-therapeutic amount and the cancer is a renal cell cancer (RCC) and the at least one additional API is selected from etinostat, bevacizumab, IL-2, vorinostat, and CB-839 (glutaminase inh).

In embodiments, the amount of the HSP90 inhibitor is a sub-therapeutic amount and the cancer is pancreatic cancer and the at least one additional API is galunisertib.

In embodiments, the amount of the HSP90 inhibitor is a sub-therapeutic amount and the cancer is gastric cancer and the at least one additional API is selected from trastuzumab, capecitabine, cisplatin, margetuximab, and apatinib.

In embodiments, the amount of the HSP90 inhibitor is a sub-therapeutic amount and the cancer is liver cancer and the at least one additional API is selected from apatinib, and sorafenib.

In embodiments, the amount of the HSP90 inhibitor is a sub-therapeutic amount and the cancer is myelodysplastic syndrome (MDS) and the at least one additional API is selected from azacytidine, tremelimumab, and etinostat.

In embodiments, the amount of the HSP90 inhibitor is a sub-therapeutic amount and the cancer is chronic lymphocytic leukemia (CLL) and the at least one additional API is selected from obinutuzumab, ibrutinib, lenalidomide, rituximab, and bendamustine.

In embodiments, the amount of the HSP90 inhibitor is a sub-therapeutic amount and the cancer is metastatic colorectal or prostate cancer and the at least one additional API is selected from sipuleucel-T, enzalutamide, olaparib, docetaxel, prednisone, and dexamethasone.

In embodiments, the amount of the HSP90 inhibitor is a sub-therapeutic amount and the cancer is diffuse large B cell lymphoma (DLBCL) and the at least one additional API is selected from KTE-19, AZD9150 (STAT3 inh), utomilumab, rituximab, azacytidine, bendamustine, gemcitabine, oxaliplatin, and R-CHOP.

In embodiments, the amount of the HSP90 inhibitor is a sub-therapeutic amount and the cancer is a glioblastoma and the at least one additional API is selected from urelumab (anti-4-1BB) and BMS 986016 (Anti-LAG-3).

In embodiments, the amount of the HSP90 inhibitor is a sub-therapeutic amount and the cancer is multiple myeloma (MM) and the at least one additional API is selected from lenalidomide, dexamethasone, carfilzomib, daratumumab (anti-CD38), and pomalidomide.

In embodiments, the amount of the HSP90 inhibitor is a sub-therapeutic amount and the cancer is a gastrointestinal or thoracic cancer and the at least one additional API is ramucirumab (anti-VEGFR2).

In embodiments, the amount of the HSP90 inhibitor is a sub-therapeutic amount and the cancer is a head and neck cancer and the at least one additional API is selected from cisplatin/carboplatin, 5FU, cetuximab, and SD-101 (anti-TLR9).

In embodiments, the amount of the HSP90 inhibitor is a sub-therapeutic amount, the cancer is acute myeloid leukemia (AML) and the at least one additional API is selected from azacytidine, crenolanib, cytarabine, daunorubicin, etoposide, gilteritinib, guadecitabine, idarubicin, midostaurin, mitoxantrone, quizartinib, sorafenib, tandutinib, and venetoclax. In embodiments, the at least one additional API is selected from crenolanib, cytarabine, daunorubicin, gilteritinib, sorafenib, and venetoclax. In embodiments, the at least one additional API is venetoclax. In embodiments, the at least one additional API is selected from an anthracycline, such as daunorubicin, doxorubicin, epirubicin, mitoxantrone, and idarubicin; cytarabine; a tyrosine kinase inhibitor (TKI) such as midostaurin, sorefenib, crenolanib, quizartinib, tandutinib, gilteritinib, lestaurtinib, dovitinib, pacritinib, and XL999; etoposide, fludarabine, G-CSF, azacytidine, decitabine, venetoclax, ABT-737, navitoclax, obatoclax, sabutoclax, S 55746, AT-101 (Gossypol), and APG-1252, and combinations of any of the foregoing. In embodiments, the at least one additional API is selected from arsenic trioxide (trisenox), cerubidine (Daunorubicin Hydrochloride), clafen (Cyclophosphamide), cyclophosphamide, cytarabine (tarabine PFS), cytosar-U (Cytarabine), cytoxan (Cyclophosphamide), daunorubicin hydrochloride (rubidomycin), doxorubicin hydrochloride, enasidenib mesylate, idamycin (idarubicin hydrochloride), idarubicin hydrochloride idhifa (Enasidenib Mesylate), midostaurin (Rydapt), mitoxantrone hydrochloride, neosar (Cyclophosphamide), thioguanine (Tabloid), vincristine sulfate (vincasar PFS), azacytidine, and decitabine, and combinations of any of the foregoing. In embodiments, the at least one additional API is a PD-1/PD-L1 inhibitor selected from the group consisting of AMP-224, AMP-514/MEDI-0680, atezolizumab (MPDL3280A), avelumab (MSB0010718C), BGB-A317, BMS936559, cemiplimab (REGN2810), durvalumab (MEDI-4736), JTX-4014, nivolumab (BMS-936558), pembrolizumab (Keytruda, MK-3475), GLS-010 and SHR-1210. In embodiments, the at least one additional API is a BCL-2 pathway inhibitor selected from the group consisting of ABT-737, AT-101 (Gossypol), APG-1252, A1155463, A1210477, navitoclax, obatoclax, sabutoclax, venetoclax, S 55746, and WEHI-539. In embodiments, the BCL-2 pathway inhibitor is an inhibitor of BCL2, BCLXL, or MCL1. In embodiments, the BCL-2 pathway inhibitor is selected from AMG-176, MIK665 and S641315. In embodiments, the BCL-2 pathway inhibitor is selected from ABT-737, navitoclax, and venetoclax.

In embodiments, the amount of the HSP90 inhibitor is a sub-therapeutic amount and the cancer is melanoma and the at least one additional API is selected from dabrafenib, trametinib, PLX3397 (CSF-R1 inh), vemurafenib, IFNα2B, dacarbazine, carboplatin, paclitaxel, and SD-101 (anti-TLR9).

In embodiments, the amount of the HSP90 inhibitor is a sub-therapeutic amount and the cancer is non-Hodgkins lymphoma and the at least one additional API is selected from JCAR014.

In embodiments, the amount of the HSP90 inhibitor is a sub-therapeutic amount, the cancer is a renal cancer, and the anti-cancer agent may be selected from a VEGF inhibitor such as sunitinib, pazopanib, bevacizumab, sorafenib, cabozantinb and axitinib or an mTOR inhibitor such as everolimus or temsirolimus.

Generally, where two different APIs are administered, one is considered the primary agent and the other is an adjunct to the primary agent. In embodiments of the methods described here, the HSP90 inhibitor may be either the primary or adjunct agent in the therapeutic regimen. In embodiments, the adjunct agent is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the primary agent in the therapeutic regimen.

In the context of the methods described herein, the amount of an HSP90 inhibitor administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject. In embodiments, the therapeutically effective amount of an HSP90 inhibitor in the methods described here is a dose that would be considered 'sub-therapeutic' or below the dose expected to be effective based on phase 2 clinical studies of the HSP90 inhibitor. In embodiments, a sub-therapeutic dose of an HSP90 inhibitor is a dose that is less than 75% of the recommended phase 2 dose of the HSP90 inhibitor, or less than 50%, or less than 25% of the recommended phase 2 dose of the HSP90 inhibitor. In one embodiment, the therapeutically effective amount of an HSP90 inhibitor is the amount effective to inhibit IFN-γ signaling in cancer cells of the subject. In embodiments, the methods comprise administering a sub-therapeutic dose of an HSP90 inhibitor, alone or in combination with one or more additional APIs.

As used herein, "treatment", "treating" or "treat" describes the management and care of a patient for the purpose of combating a disease, condition, or disorder and includes the administration of an HSP90 inhibitor, alone as monotherapy (for example, utilizing low dose HSP90) or in combination with at least one additional API as described here, to alleviate the symptoms or complications of a disease, condition or disorder, or to eliminate the disease, condition or disorder.

In embodiments, including both monotherapy with an HSP90 inhibitor and combination therapies with one or more additional APIs, the administration of an HSP90 inhibitor leads to the elimination of a symptom or complication of the cancer being treated, however elimination of the cancer is not required. In one embodiment, the severity of the symptom is decreased. In the context of cancer, such symptoms may include clinical markers of severity or progression including the degree to which a tumor secretes growth factors, degrades the extracellular matrix, becomes vascularized, loses adhesion to juxtaposed tissues, or metastasizes, as well as the number of metastases and reduction in tumor size and/or volume.

Treating cancer according to the methods described herein can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer according to the methods described herein can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer according to the methods described herein can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×. For hematologic cancers, the count may be the number of cells related to the cancer (e.g., lymphoma or leukemia cells) in a sample of blood.

Treating cancer according to the methods described herein can result in a decrease in the number of metastatic lesions in other tissues or organs distant from the primary tumor site. Preferably, after treatment, the number of metastatic lesions is reduced by 5% or greater relative to the number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer according to the methods described herein can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment. An increase in average survival time of a population may also be measured, for example, by calculating for a population the average length of survival following completion of a first round of treatment.

Treating cancer according to the methods described herein can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment. An increase in average survival time of a population may also be measured, for example, by calculating for a population the average length of survival following completion of a first round of treatment.

Treating cancer according to the methods described herein can result in an increase in average survival time of a population of treated subjects in comparison to a population receiving monotherapy with a drug that is not an HSP90 inhibitor. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment. An increase in average survival time of a population may also be measured, for example, by calculating for a population the average length of survival following completion of a first round of treatment.

Treating cancer according to the methods described herein can result in a decrease in the mortality rate of a population of treated subjects in comparison to a population receiving carrier alone. Treating a disorder, disease or condition according to the methods described herein can result in a decrease in the mortality rate of a population of treated subjects in comparison to an untreated population. Treating a disorder, disease or condition according to the methods described herein can result in a decrease in the mortality rate of a population of treated subjects in comparison to a population receiving monotherapy with a drug that is not an HSP90 inhibitor. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment. A decrease in the mortality rate of a population may also be measured, for example, by calculating for a population the average number of disease-related deaths per unit time following completion of a first round of treatment.

Treating cancer according to the methods described herein can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time. In one embodiment, after treatment the tumor growth rate may be about zero and is determined to maintain the same size, e.g., the tumor has stopped growing.

Treating cancer according to the methods described herein can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Pharmaceutical Compositions and Formulations

The present disclosure provides pharmaceutical compositions comprising an amount of an HSP90 inhibitor, either alone or in combination with at least one additional API, such as a BCL-2 pathway inhibitor. In embodiments, the amount of the HSP90 inhibitor is less than 75% of the recommended phase 2 dose of the HSP90 inhibitor. In embodiments, the amount of the HSP90 inhibitor is less than 75% of the recommended phase 2 dose of the HSP90 inhibitor. In accordance with any of the embodiments described here, the pharmaceutical composition may be adapted for oral, buccal, or parenteral administration. In embodiments, the pharmaceutical composition may be adapted for pulmonary administration, for example by inhalation. In embodiments, the pharmaceutical composition is adapted for oral administration. In embodiments, the pharmaceutical composition is adapted for parenteral administration.

In embodiments, the HSP90 inhibitor is combined with at least one additional API in a single dosage form. In embodiments, the at least one additional API is selected from an agent described supra in connection with methods of treatment using combination therapy.

A "pharmaceutical composition" is a formulation containing the compounds described herein in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in m², and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In embodiments, the disclosure provides the following.

1. A pharmaceutical composition comprising an HSP90 inhibitor, and a pharmaceutically acceptable carrier or excipient, for use in treating cancer in a subject in need thereof, wherein the composition comprises an amount of the HSP90 inhibitor that is less than 75% of the recommended phase 2 dose of the HSP90 inhibitor.

2. A method for treating cancer in a subject in need thereof, comprising administering to the subject a pharmaceutical composition comprising an amount of an HSP90 inhibitor, and a pharmaceutically acceptable carrier or excipient, wherein the amount of the HSP90 inhibitor is less than 75% of the recommended phase 2 dose of the HSP90 inhibitor.

3. The method of claim 1 or 2, wherein the amount of the HSP90 inhibitor is less than 50% or less than 25% of the recommended phase 2 dose of the HSP90 inhibitor.

4. The method of any one of claims 1-3, wherein the HSP90 inhibitor is selected from the group consisting of HSP-990, CNF-2024, PF0498473, tanespimycin, STA-9090, MPC-3100, CUDC-305, XL-888, TAS-116, and pharmaceutically acceptable salts thereof.

5. The method of any one of claims 1-3, wherein the HSP90 inhibitor is selected from the group consisting of tanespimycin, alvespimycin, IPI-504, AUY922, AT13387, ganetespib, KW-2478, CNF2024, MPC3100, BIIB028, SNX5422, PU-H71, MPC-0767, and pharmaceutically acceptable salts thereof.

6. The method of any one of claims 1-5, wherein the pharmaceutical composition comprises a second active pharmaceutical ingredient (API).

7. The method of claim 6, wherein the second API is selected from an HDAC inhibitor, an ImiD, an anti-VEGFR antibody, a DNA methylation inhibitor, a steroid hormone (ant)agonist, a metabolic enzyme inhibitor, a proteasome inhibitor, an anti-CD20 antibody, an adenosine receptor 2A antagonist, a toll-receptor (ant(agonist), an immunostimulatory cytokine, and combinations thereof.

8. The method of claim 6, wherein the second API is selected from cisplatin, docotaxel, gemcitabine, carboplatin, paclitaxel, pemetrexed, etoposide, epirubicin, doxorubicin, cyclophosphamide, ddAC, everolimus, panobinostat, exemestane, letrozole, decitabine, esartinib, abemacicib, merestinib, gefitinib, mocetinostat, azacytidine, etinostat, motolimod, ibrutinib, lenalidomide, idelalisib, enzalutamide, olaparib, prednisone, dexamethasone, vinflunine, vorinostat, galunisertib, bendamustine, oxaliplatin, leucovorin, guadecitabine, dabrafenib, trametinib, vemurafenib, dacarbazine, apatinib, pomalidomide, carfilzomib, sorafenib, 5-fluorouracil, CB-839, CB-1158, GDC-0919, LXH254, AZD4635, AZD9150, PLX3397, LCL161, PBF-509, bevacizumab, Sym004, ramucirumab, ipilimumab, trastuzumab, tremelimumab, obinutuzumab, B-701, utomilumab, rituximab, bevacizumab, interleukin 2, NKTR-214, denenicokin, PEGlnterferon 2A, RO7009789, MEDI9447, MK-1248, LY2510924, ARRY-382, MEDI0562, LAG525; NIS793, Lirilumab, varlilumab, GWN323; JTX-2011; Galunisertib; TSR-022; BMS-986016, ramucirumab, urelumab, BMS-986016, and REGN3767.

9. The method of claim 6, wherein the second API in the composition is selected from the group consisting of a protein kinase inhibitor, a PD-1/PD-L1 inhibitor, a checkpoint inhibitor, a platinum based anti-neoplastic agent, a topoisomerase inhibitor, a nucleoside metabolic inhibitor, an alkylating agent, an intercalating agent, a tubulin binding agent, an inhibitor of DNA repair, and combinations thereof.

10. The method of claim 9, wherein the second API in the composition is a PD-1/PD-L1 inhibitor.

11. The method of claim 10, wherein the PD-1/PD-L1 inhibitor is selected from the group consisting of nivolumab, pembrolizumab, AMP-514/MEDI-0680, atezolizumab, durvalumab, avelumab, BMS936559, AMP-224, BGB-A317, SHR-1210, and JTX-4014.

12. The method of claim 10 or 11, wherein the amount the PD-1/PD-L1 inhibitor is less than 75% of the recommended phase 2 dose of the PD-1/PD-L1 inhibitor.

13. The method of claim 6, wherein the second API in the composition is a CTLA-4 inhibitor.

14. The method of claim 13, wherein the CTLA-4 inhibitor is selected from tremlimumab and ipilimumab.

15. The method of claim 9, wherein the second API in the composition is a checkpoint inhibitor.

16. The method of claim 15, wherein the checkpoint inhibitor is selected from the group consisting of an anti-CD27 antibody, an anti-B7-H3 antibody, an anti-KIR antibody, an anti-LAG-3 antibody, an anti-TIM3 antibody, an anti-OX40 antibody, an anti-4-1BB/CD137 antibody, an anti-CD40 antibody, an anti-TRX518 antibody, an anti-CD73 antibody, and an anti-GITR antibody.

17. The method of claim 15, wherein the checkpoint inhibitor is selected from the group consisting of varlilumab, MGA217, lirilumab, BMS-986016, urelumab, MEDI-0562, SEA-CD40, TRX518, and MK-4166.

18. The method of claim 9, wherein the second API in the composition is a DNA repair inhibitor selected from the group consisting of olaparib, rucaparib, niraparib, talazoparib veliparib, CEP-9722, and CEP-8983.

19. The method of any one of claims 1-18, wherein the cancer is selected from the group consisting of brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, head and neck cancer, gastrointestinal cancer, hepatocellular carcinoma, gallbladder cancer, esophageal cancer, gastric cancer, colorectal cancer, pancreatic cancer, neuroendocrine tumors, thyroid tumor, pituitary tumor, adrenal tumor, a T-cell lymphoma, non-Hodgkin's lymphoma, mantle cell lymphoma, multiple myeloma, B-cell lymphoma, leukemia, and Hodgkin's lymphoma.

20. The method of claim 19, wherein the cancer is selected from the group consisting of melanoma, Hodgkin's lymphoma, non-small cell lung cancer, bladder cancer, non-Hodgkin's lymphoma, leukemia, T-cell lymphoma, and renal cell carcinoma.

21. The method of claim 10, 11, or 12, wherein the cancer is selected from the group consisting of melanoma, Hodgkin's lymphoma, non-small cell lung cancer, bladder cancer, non-Hodgkin's lymphoma, leukemia, T-cell lymphoma, and renal cell carcinoma.

22. The method of any one of claims 1-21, wherein the pharmaceutical composition comprises an amount of an HSP90 inhibitor effective to inhibit interferon-γ signal transduction in cancer cells of the subject.

23. The method of any one of claims 1-22, wherein the subject is human.

24. The method of any one of claims 1-23, wherein the pharmaceutical composition is adapted for oral or buccal administration.

25. The method of any one of claims 1-23, wherein the pharmaceutical composition is adapted for parenteral administration.

EXAMPLES

Example 1—A Screen to Identify Small Molecule Inhibitors of PD-L1 Cell Surface Expression SK-MEL-28 cells (melanoma cell line; ATCC® HTB-72™) were used to conduct a high-content screen to identify small molecules that reduce interferon-gamma (IFN-γ) (Shenandoah Biotechnology) induced PD-L1 expression.

Cells were expanded in MEM (Corning) containing 10% FBS (Sigma) and 2 mM L-Glutamine. Frozen stocks of cells were prepared for direct use in the high-throughput screening (HTS) assay. Cells were harvested, pelleted and then resuspended in 95% FBS & 5% DMSO at a concentration $1 \times 10^7$ cells/ml. One ml aliquots were rate frozen to −80° C. at a rate of 1 degree per minute. These stocks were then transferred to vapor phase liquid nitrogen for long term storage.

For screening, frozen cell vials were quickly thawed with continuous agitation in a at 37° C. water bath then resuspended in the assay media at room temperature and centrifuged at 1,000 rpm for 5 minutes. The resulting pellet was re-suspended in appropriate volume and counted using an automated cell counter and diluted accordingly.

Using a manually curated library of approximately 2500 individual drugs (2000 approved drugs, 500 unapproved drugs), drugs from the source plate were transferred to the destination plates (384-well assay plates—Corning #3712) using an ECHO 550 liquid handler (Labcyte). SK-MEL-28 cells (1750 cells per well in 30 μL of media), treated with IFN-g (50 ng/ml final) were added to these pre-formatted plates using a Multidrop™ Combi reagent dispenser (Thermofisher). The final concentration of the drugs was 40, 480 and 5000 nM. The outer 2 columns on the left of the plate and the right of the plate (columns 1, 2, 23, 24) served as positive and negative controls and were treated with and without IFN-γ, respectively. Plates were centrifuged at 800 rpm for one minute before being incubated in a 5% $CO_2$ humidified incubator at 37° C.

44 h later, cell viability was determined using alamarBlue™ cell viability reagent (Thermofisher), according to the manufacturers protocol. Briefly, 3 µL of alamarBlue™ reagent was added to each well and plates were incubated for a further 4 h. The plates were read on a Victor $^3$V plate reader (Perkin Elmer). Viability for each drug was expressed as a percentage by comparing drug-treated cells and untreated control cells (Set to 100%).

After assessment for viability, plates were then prepared for immunostaining. Briefly, 16% paraformaldehyde (Electron Microscopy Sciences) was added to each well to a final concentration of 4%, for 10 minutes at room temperature. Following this time, the fix was aspirated and cells were washed 3 times with PBS. Cells were blocked using blocking solution (1% bovine serum albumin in PBS) for 30 minutes. After this time, the blocking reagent was aspirated and immunostaining reagent added. The immunostaining reagent consisted of a biotin conjugated-PD-L1 antibody (eBioscience) diluted in blocking buffer. Plates were sealed and kept at 4 C overnight. The following day, plates were washed 3 times with PBS followed by addition of a streptavidin-luciferase fusion protein (Invivogen) diluted in blocking buffer, for 1 h at room temperature. After this step, the plates were washed 3 times with PBS. After the final wash, PBS was aspirated and 30 uL of QUANTI-Luc™ (Invivogen) was added per well. Plates were immediately read on a plate reader (Victor 3V plate reader, 0.1s) and luciferase activity measured.

The raw PD-L1 intensity (the luciferase readout) corresponding to drug screen plates was normalized to blank plates containing only IFN-γ-treated wells, and the resulting ratio was used for the calculation of Z-scores.

The Z-scores were calculated for each drug taking into account the blank-corrected PD-L1 intensity and the control +IFN-γ-treated wells in each drug plate, according to the following equation:

$$Zscore = \frac{I^{Drug} - \text{mean}(I^{+IFN})}{sd(I^{+IFN})}$$

where $I^{Drug}$ is the blank-corrected PD-L1 intensity for each drug. Therefore, Z score values will be negative for those drugs that decrease PD-L1 levels with respect to the IFN-γ-treated wells.

In order to compare the PD-L1 effect of different drug doses tested across different plates, we defined a relative Z score, that takes into account the drug Z score and the distribution of Z scores corresponding to the IFN-γ untreated control wells.

$$\text{relative } Zscore = \frac{Zscore^{Drug}}{\text{mean}(Zscore^{-IFN})}$$

The relative Z score is a measure of drug PD-L1 level effect with respect to the baseline PD-L1 signal.

Once we computed the relative Z scores for all drugs and all concentrations tested in the screen, we applied three filtering criteria to narrow down drug list and select high-confidence hits, as follows:
1 Select drugs with a relative Z score $<=-1+sd$ (Z score$^{-IFN-\gamma}$) and a viability percent >75% for the three concentrations tested. This rendered 10 drugs at 40 nM, 27 drugs at 480 nM and 196 drugs at 5000 nM (out of 4126 total drugs).
2 Select drugs at 5000 nM that showed a hit percent >50%. This resulted in 110 drugs at 5000 nM (out of 196 obtained in #1).
3 Select drugs that showed a dose-responsive relative Z score. This resulted in 47 drugs.

To summarize the results from the primary screen, 47 drugs reduced IFN-γ-induced PD-L1 expression. Notably, these included small molecule inhibitors of JAK2, which have previously been shown to abrogate PD-L1 expression (Green et al., 2010).

Of the 47 drug identified in the primary screen, we focused our efforts on the HSP90 inhibitor class of drugs since there were 4 individual small molecule inhibitors targeting HSP90 in our library of ~2500 drugs (HSP-990, CNF-2024, PF0498473 and tanespimycin), and all 4 were identified as hits in the primary screen.

These 4 HSP90 inhibitors were validated using the same experimental protocol employed above (using the SK-MEL-28 cells +/-IFN-γ in 384 well plates), with the only exception to the original assay design was that each drug was now tested in a 10-point dose response assay where the concentration of drug tested was 9.8-5000 nM (2 fold serial dilution). Cells were seeded and treated in quadruplicate. Viability was assessed after 48 h of treatment of four HSP 90 inhibitors and prior to harvesting the cells for testing PD-L1 signal, as described above.

In this secondary assay all 4 HSP90 drugs (HSP-990, CNF-2024, PF0498473 and tanespimycin) were validated by confirming that IFN-γ-induced PD-L1 signal was blocked (FIG. 1A-D).

Thus, these findings serve to demonstrate that we have uncovered a mechanistic link between inhibition of HSP90 and abrogating IFN-γ-induced PD-L1 expression.

Previous studies noted that inhibition of HSP90 reduced JAK2 levels and suggested JAK2 could be a client protein of HSP90 (Marubayashi et al., 2010)(Proia et al., 2011). However, to date, no direct link of HSP90 inhibition and PD-L1 expression has been made. The results reported here suggest that HSP90 inhibitors can have a therapeutic effect by modulating the immune response toward instances where the PD-1/PD-L1 axis is usurped to evade immune surveillance. This mechanism can be exploited, as described herein, to provide a new approach to cancer treatment using low dose HSP90 inhibitors, alone or in combination with other active agents.

When comparing the concentrations at which the HSP90 inhibitors exerted their immuno-modulatory effects on PD-L1 versus their anti-proliferative effects, it was evident that the effects of HSP90 inhibitors on inhibition of IFN-γ-induced PD-L1 expression occurred at concentrations much lower than those required for anti-proliferative activity (see FIG. 1A-D).

We therefore sought to extend the preliminary findings from our HTS screen by testing additional HSP90 inhibitors not present in our library of ~2500 drugs. STA-9090, MPC-3100, CUDC-305, XL-888 and TAS-116, were tested for their ability to inhibit IFN-γ-induced PD-L1 expression. As shown in FIG. 2A-E, the 5 additionally tested HSP90 inhibitors showed the same trend—the concentration required to inhibit IFN-γ-induced PD-L1 expression (red line) was far lower than the concentration required to affect cell proliferation since cell viability remained higher than 80% at the highest concentration tested (1000 nM).

Figure 3:
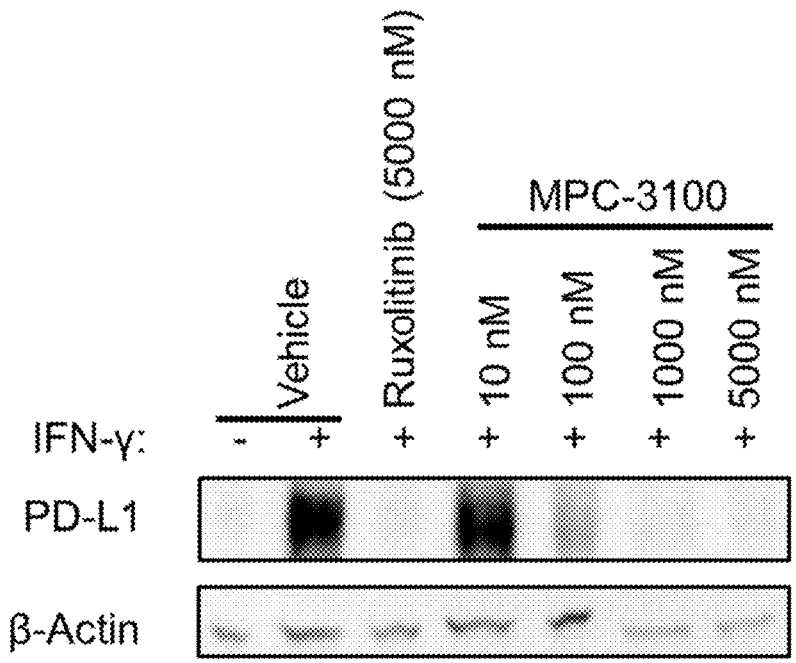
FIG. 3. Effect of the HSP90 inhibitor MPC-3100 on the IFN-γ-induced PD-L1 protein expression. Human HCC-38 cells treated with IFN-γ alone or co-treated with ruxolitinib (5000 nM) or MPC-3100 (10-5000 nM) for 48 h were analyzed by Western blot analysis to determine protein expression levels of PD-L1. Ruxolitinib served as a positive control for inhibiting JAK2. β-Actin was used as a loading control.

To confirm that our findings are applicable to other cell types, an additional human breast cancer cell line HCC-38 was used. HCC-38 cells were treated with IFN-γ (50 ng/ml) and co-treated with MPC-3100 at 10, 100, 1000 and 5000 nM for 48 h. As shown in FIG. 3, IFN-γ-induced PD-L1 expression was reduced by MPC-3100 at 100 nM and was completely abrogated at 1000 nM.

Considering the maximum concentration (Cmax, geometric mean) of MPC-3100 in the patients' plasma dosed at the recommended phase 2 dose is ~13 µM, the concentrations at which MPC-3100 elicited immuno-modulatory activity toward PD-L1 is at least 10 fold lower.

Figure 4A:
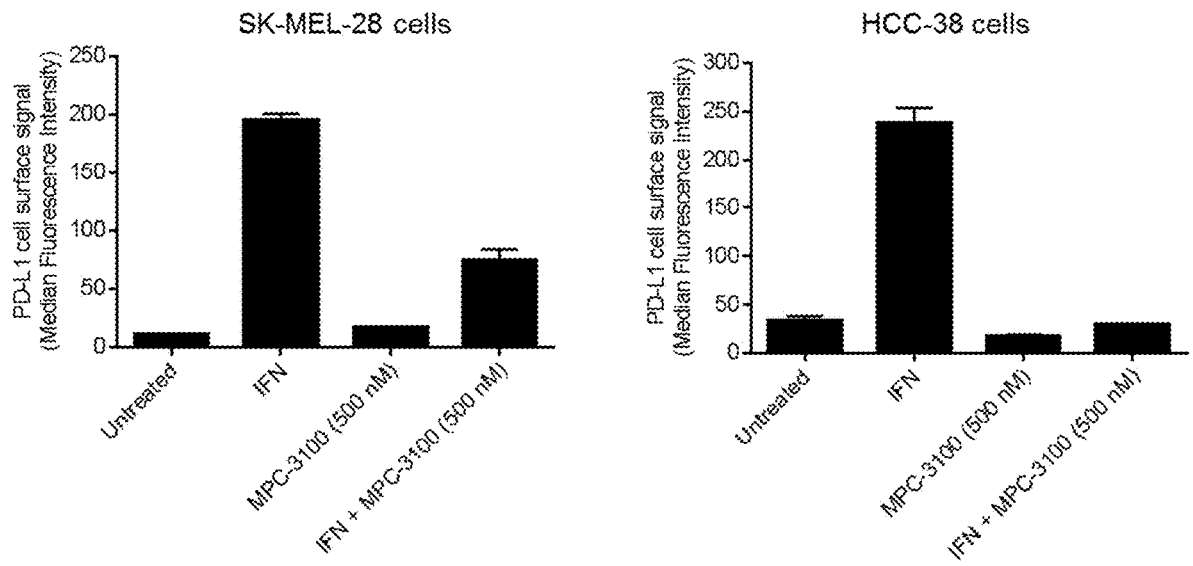
FIG. 4A-B. Effect of the HSP90 inhibitor MPC-3100 on the IFN-γ-induced PD-L1 surface signal. A) SK-MEL-28 and HCC-38 (both human lines) were treated with IFN-γ (50 ng/ml), MPC-3100 (500 nM or 1000 nM) or the combination for 48 h. B) EMT-6 and B16-F10 (both murine cell lines) were also treated with IFN-γ, MPC-3100 or the combination for 24 h. PD-L1 cell surface signals were analyzed by flow cytometry. Experiments were performed in duplicate and at least 2 independent times.
Figure 4B:
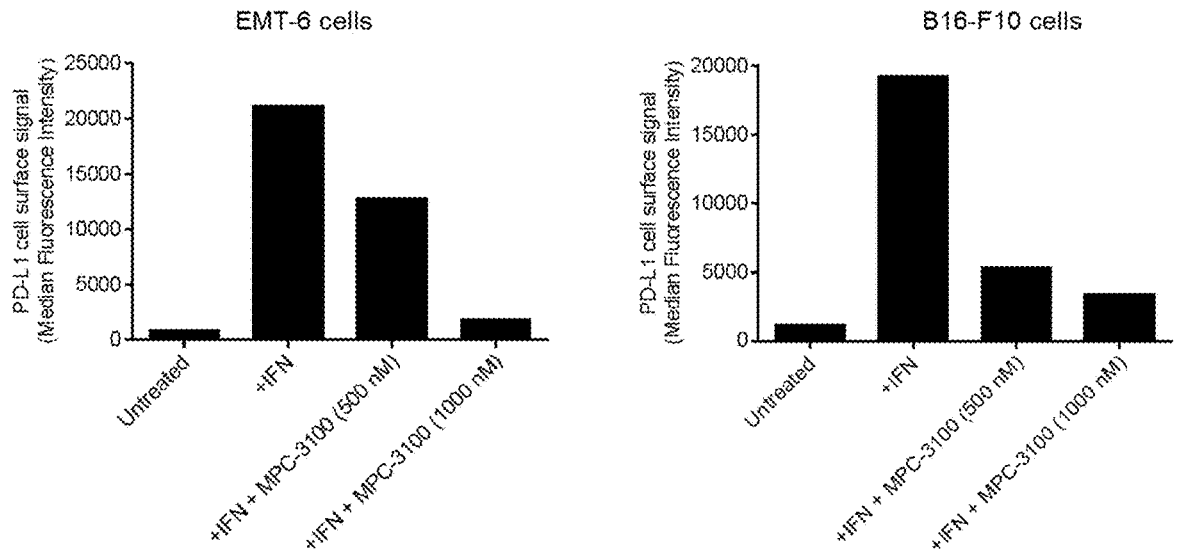

To verify that the activity of MPC-3100 on abrogating IFN-γ-induced PD-L1 expression as detected by western blotting, which measures total intracellular protein, resulted in decreased cell surface expression, flow cytometry was performed. Two human cell lines were used (SK-MEL-28 and HCC-38 cells) and two murine cell lines were used (B16-F10, a melanoma cell line and EMT-6, a breast cancer cell line). All cells lines were treated with IFN-γ (50 ng/nl) and co-treated with MPC-3100 at the indicated concentrations for 48 h. As shown in FIG. 4A-B, all cell lines tested showed that MPC-3100 effectively inhibited IFN-γ-induced cell surface expression of PD-L1.

Figure 5:
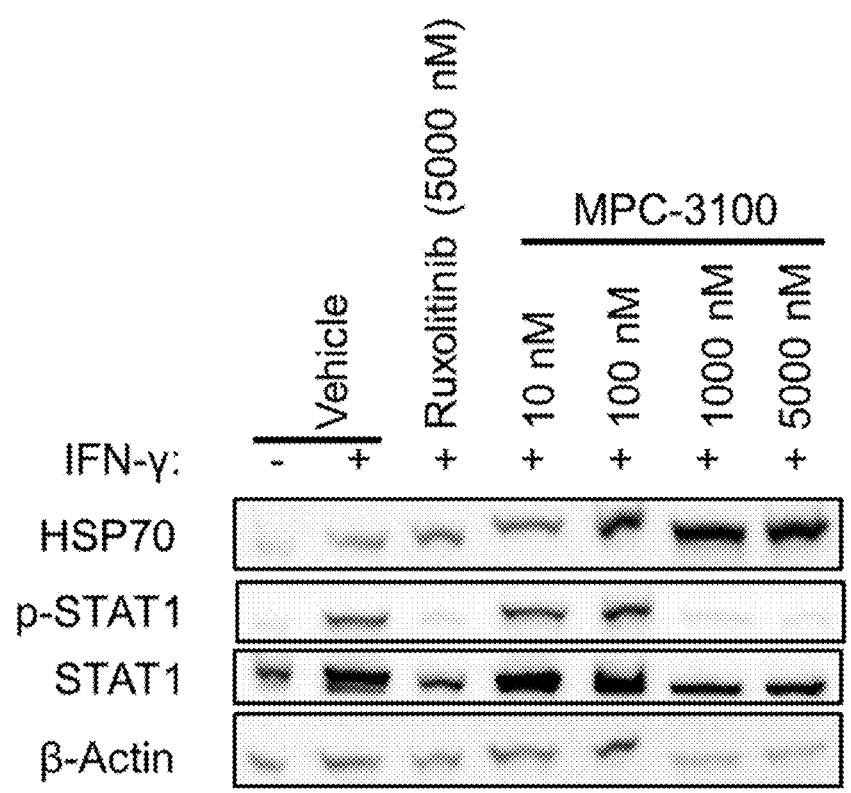
FIG. 5. HCC-38 cells treated with IFN-γ alone or co-treated with ruxolitinib (5000 nM) or MPC-3100 (10-5000 nM) were analyzed by Western blot to determine protein expression levels of HSP70 and pSTAT1. β-Actin was used as a loading control.

Since IFN-γ stimulates the expression of its target genes, such as PD-L1, which is mediated via JAK/STAT-1 signaling, the human HCC-38 cell line was used to probe the mechanism for IFN-γ-induced PD-L1 expression. As shown in FIG. 5, MPC-3100 blocks IFN-γ-induced p-STAT1, suggesting this is the mechanism for how MPC-3100 blocks IFN-γ-induced PD-L1 expression. Again, the concentrations at which this occurred was at least 10 fold lower than the Cmax at the recommended Phase 2 dose of the drug.

Consistent with the findings above, the drug ruxolitinb, (a JAK2 inhibitor) also blocked IFN-induced PD-L1 expression through its inhibitory activity toward JAK2, as measured by inhibition of p-STAT.

Numerous studies have shown that exposing cells to HSP90 inhibitors results in a paradoxical increase in HSP70 expression, both in vitro and in vivo. As shown in FIG. 5, HCC-38 cells treated with MPC-3100 also show an increase in HSP70 expression.

Figure 6:
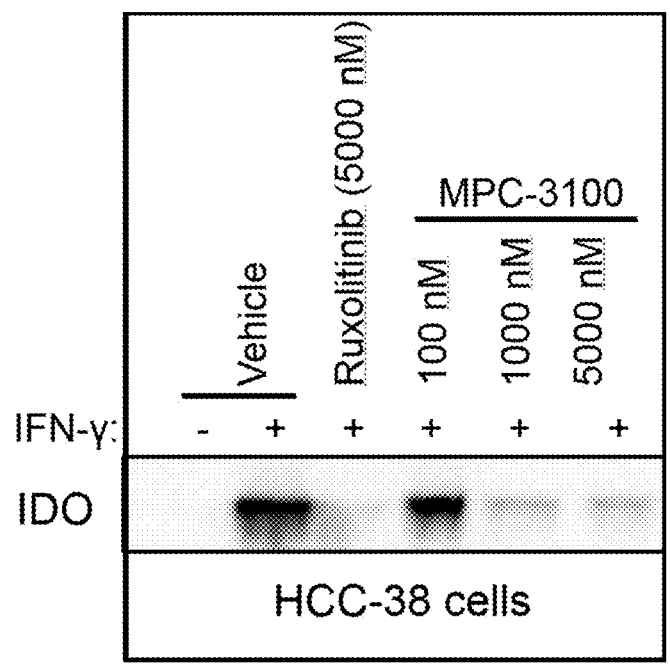
FIG. 6. Effect of HSP90 inhibitor MPC-3100 on IFN-γ-induced IDO protein levels. Human HCC-38 cells treated with IFN-γ alone or co-treated with ruxolitinib (5000 nM) or MPC-3100 (100, 1000 or 5000 nM) for 48 h. Lysates were analyzed by Western blot to determine protein expression levels of IDO.

Based on these findings, we tested whether indoleamine 2,3-dioxygenase (IDO), another IFN-γ induced protein which is implicated in immune suppression (Curti et al., 2009), can be blocked by a HSP90 inhibitor. As expected, HCC-38 cells treated with IFN-γ alone induced the expression of IDO. However, when HCC-38 cells were co-treated with IFN-γ and MPC-3100 (1000 nM or 5000 nM) IDO expression was inhibited (FIG. 6).

Collectively, these findings establish that HSP90 inhibitors, through blocking STAT-1 signaling, can effectively block IFN-γ-induced PD-L1 and IDO expression. Although HSP90 inhibitors display anti-proliferative activity, the effects on abrogating IFN-γ-induced PD-L1 expression occurs at concentrations that are not cytotoxic. This finding was demonstrated in different cell types as well as in different species, suggesting this phenomenon should be broadly translatable. Moreover, these findings show that MPC-3100 has biological activity in blocking IFN-γ-mediated signaling at concentrations that do not reduce cell viability and are also at sub-cytotoxic concentrations.

In addition to PD-L1 expression being regulated by IFN-γ in an inducible manner, several studies have shown that genetic perturbations can lead to constitutive expression of PD-L1 (Parsa et al., 2007). Indeed, glioma lines with mutations in PTEN demonstrate hyperactivation of Akt, resulting in constitutive PD-L1 expression. The levels of PD-L1 are significantly higher as compared with glioma cell lines with wild-type PTEN (Parsa et al., 2007).

Figure 7:
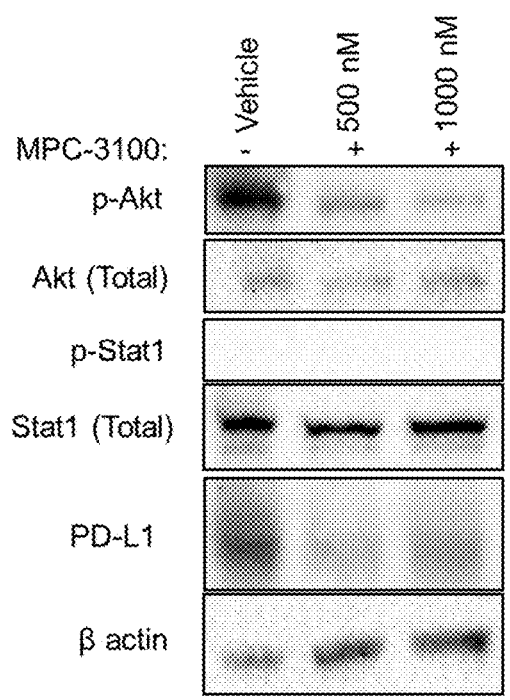
FIG. 7. Effect of HSP90-inhibitor MPC-3100 on PD-L1 protein levels. U87 cells were treated with MPC-3100 (500 and 1000 nM) for 24 h and analyzed by Western blotting with the indicated antibodies. β-Actin was used as a loading control.

To test whether HSP90 inhibitors are effective in reducing constitutive expression of PD-L1, U87 cells (human glioma) were treated with MPC-3100 at 500 or 1000 nM for 24 h. Lysates were then prepared and queried for protein expression using western blot analysis. As shown in FIG. 7, U87 cells do not have basal activation of JAK-STAT-1 signaling as evidenced by lack of detectable p-STAT. However, since these cells harbor mutant PTEN, there is hyperactivation of AKT signaling as evidenced by pAkt. Moreover, as expected from the Parsa et al. study, there is high basal expression of PD-L1. However, in U87 cells treated with MPC-3100, there is a reduction in pAkt and attenuation of PD-L1. These data demonstrate that under conditions where an oncogene induces expression of PD-L1, MPC-3100 is able to block inhibit PD-L1 expression. Furthermore, inhibition of PD-L1 expression occurs at concentrations ~10 fold lower than the therapeutic dose.

To look at whether low doses of HSP90 inhibitors exhibited higher or similar clinical efficacy than the RP2D, we performed a meta-analysis on Phase I clinical trials that included 12 different inhibitors across 20 different trials (Saif et al., 2014; Bauer et al., 2013; Siegal et al., 2011; Pacey et al., 2011; Yong et al., 2016; Reddy et al., 2013; Isambert et al., 2015; Doi et al., 2014; Padmanabhan et al., 2010; Mahadevan et al., 2012; Maddocks et al., 2016; Lancet et al., 2010; Hong et al., 2013; Solit et al., 2007; Nowakowski et al., 2006; Goldman et al., 2013; Kummar et al., 2010; Cho et al., 2011; Wagner et al., 2013; LAM Therapeutics, confidential). Only patients having stable disease for at least 4 treatment cycles or a clinical response were analyzed. The doses tested in the different trials were normalized with respect to the recommended Phase 2 dose per drug and indication and the percentage of dose (% RP2D) was calculated for each dose cohort. Patients with stable disease or clinical response across all the trials were then grouped according to the % RP2D at which they were treated, in order to calculate the percent of stable disease (% Stable Disease) and percent of response (% Response) per dose cohort across all the trials.

Figure 8:
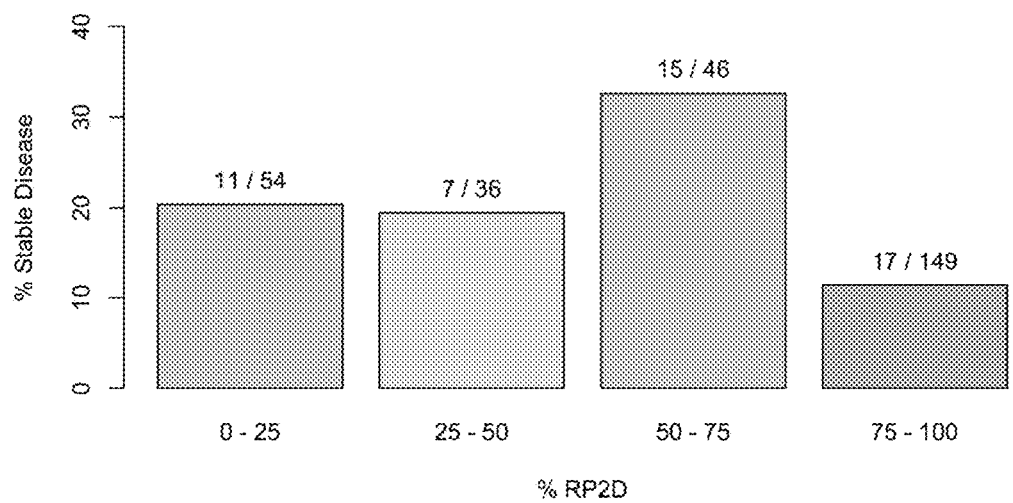
FIG. 8. Stable Disease rate per dose cohort across HSP90 inhibitor Phase I trials.
Figure 9:
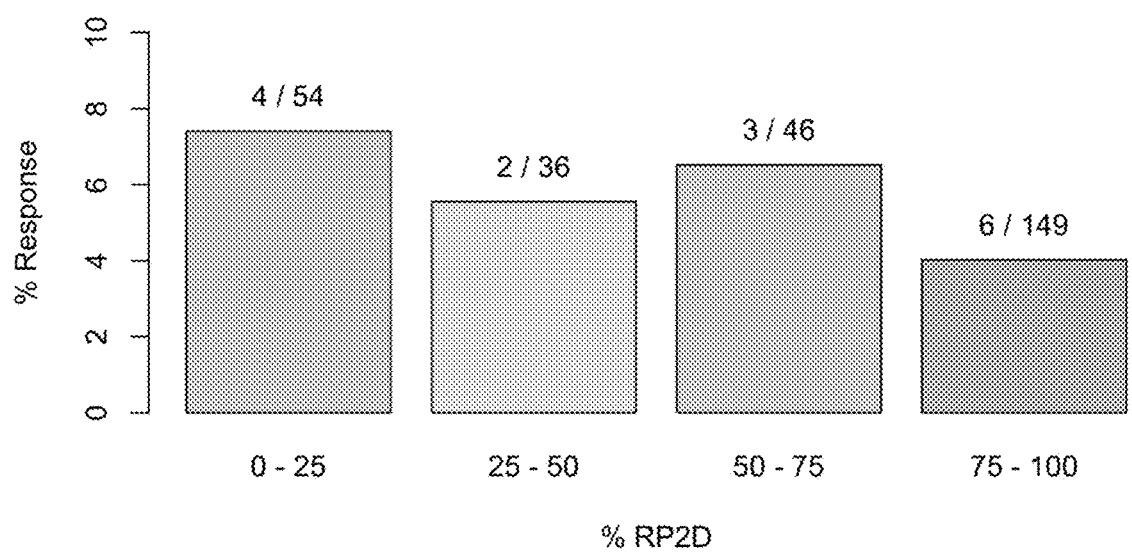
FIG. 9. Response rate per dose cohort across HSP90 inhibitor Phase I trials.
Figure 10:
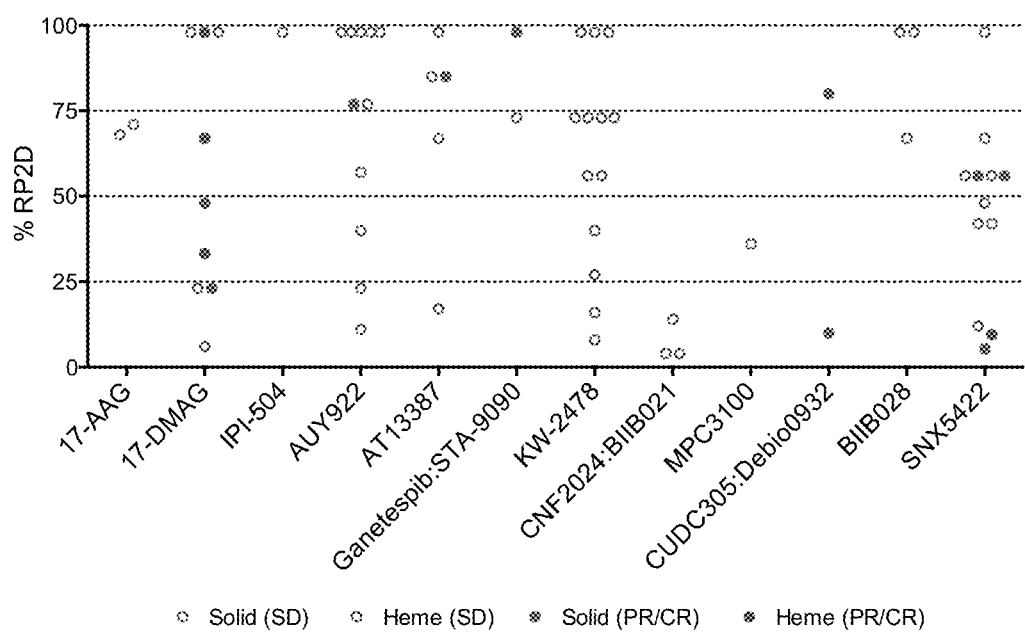
FIG. 10. Patients with stable disease or clinical response treated at different % RP2D across all HSP90 drugs that were analyzed in Phase I trials.
Figure 11A:
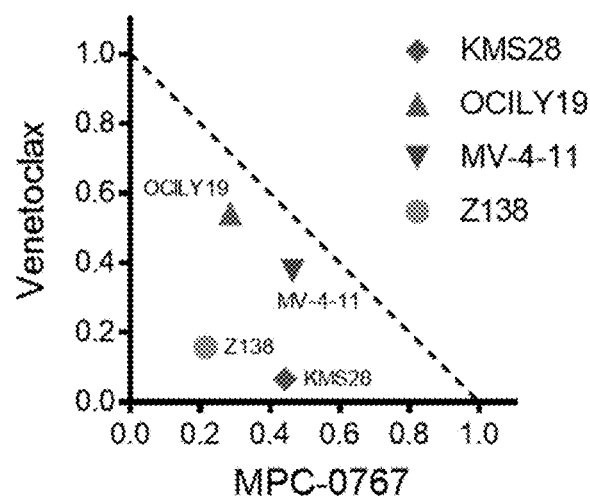
FIG. 11A-F. Normalized isobolograms at the EC75 of cell lines representing 4 different indications: Acute Myeloid Leukemia (MV-4-11), Diffuse Large B Cell Lymphoma (OCI-LY-19), Mantle Cell Lymphoma (Z138), and Multiple Myeloma (KMS-28) treated with the combination of venetoclax with each of the following HSP90 inhibitors: A) MPC-0767 B) AT13387 C) Tanespimycin D) SNX5422 E) XL-888 F) TAS-116, for 72 hours. Cell viability was assessed using CellTiter-Glo. Each data point is the average of 2 independent experiments for each cell line. Dashed line denotes 'line of additivity' whereby drug combinations below the line represent synergistic interactions.
Figure 11B:
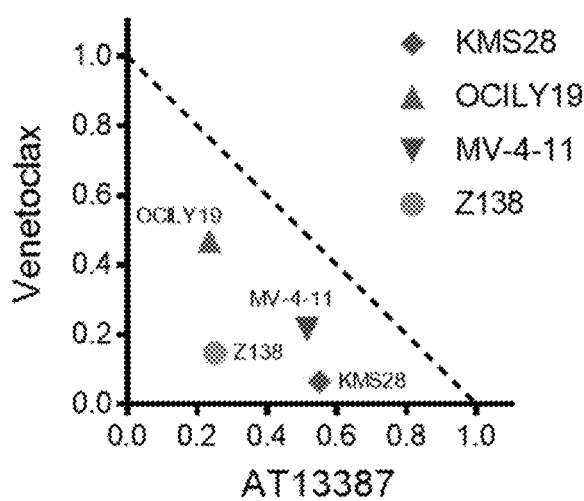
Figure 11C:
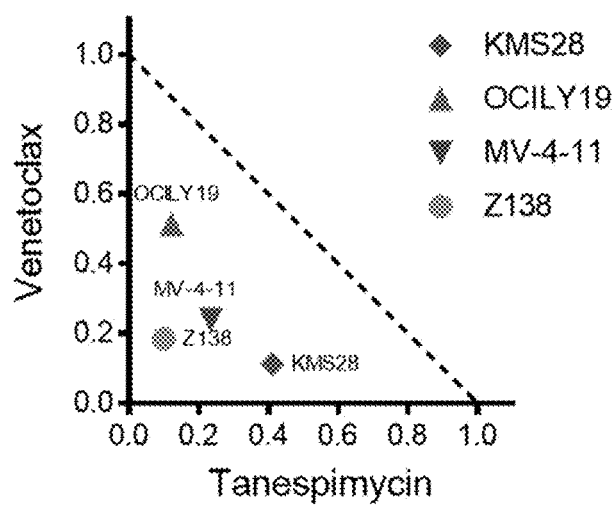
Figure 11D:
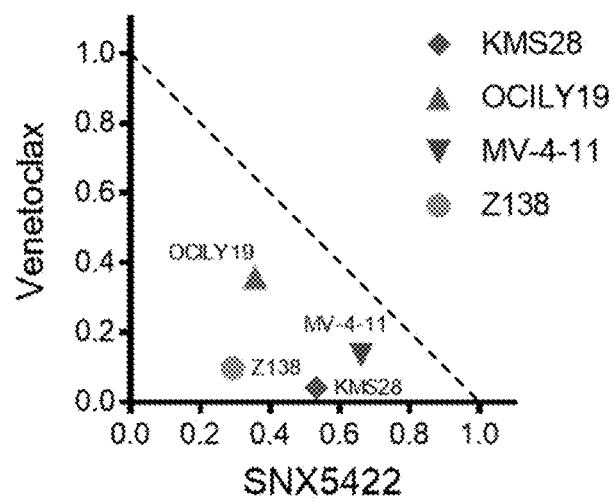
Figure 11E:
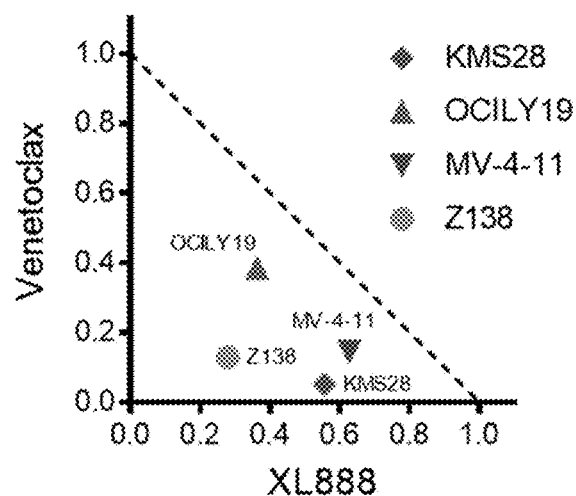
Figure 11F:
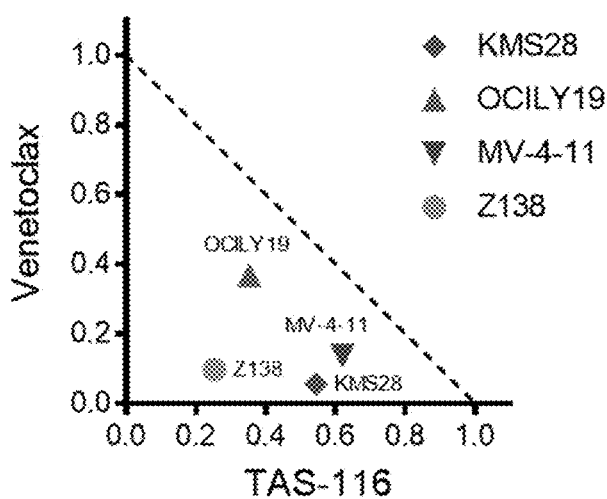

The results show that more occurrences of stable disease (FIG. 8) and clinical response (FIG. 9) are achieved at lower doses of HSP90 inhibitor than the recommended Phase 2 dose. This is when the HSP90 inhibitor is 0-25% of the RP2D, when the HSP90 inhibitor is 25-50% of the RP2D and when the HSP90 inhibitor is 50-75% of the RP2D. This observation reaches statistical significance (Fisher Test P-value=0.005) when all doses lower that 75% of the RP2D are combined. A similar trend is observed for either solid or hematopoietic and lymphoid tumors (FIG. 10), since patients with stable disease or clinical response are observed at lower doses regardless of their tumor type. Moreover our analysis suggests that the observed "low dose clinical efficacy" is a common feature of the HSP90 drug class, since all HSP90 inhibitors that were analyzed show efficacy at doses lower than the RP2D (FIG. 10). This suggests that the premise of this application should hold true for any of the HSP90 inhibitors used in the clinic.

These results support the hypothesis that HSP90 inhibitors have higher clinical efficacy when administered at lower doses thus supporting the immuno-oncology role for this drug class in cancer treatment.

Thus, collectively, the data presented for HSP90 inhibitors showing clinical activity at doses of 0-25%, 25-50%, 50-75% or 75-90% of the RP2D, could be translated into the clinic either as single agent or could reduce the dose required for combined therapies with checkpoint antibodies targeting the PD-1/PD-L1 axis. This includes antibodies that target PD-1 such as Nivolumab, Pembrolizumab, AMP-224, BGB-317 (China), SHR-1210, JTX-4014, AMP-514/MEDI-0680, GLS-010, or antibodies that target PD-L1 such as Atezolizumab, Durvalumab, Avelumab and BMS936559 (MDX-1105). Given the synergy between CTLA-4 and PD-1/PD-L1 immuno-therapies, lower dose HSP90 inhibitors maybe similarly efficacious when combined with CTLA-4 immuno-therapies such as Tremlimumab and Ipilimumab.

Cancers that have been clinically validated to show sensitivity to PD-1/PD-L1 inhibitors such as melanoma, Hodgkin lymphoma, NSCLC, bladder cancer, renal cell carcinoma may show equal sensitivity to lower dose HSP90 inhibitors.

Example 2: HSP90 Inhibitors from Different Chemical Classes Each Synergize with the Selective BCL-2 Inhibitor, Venetoclax, in their Anti-Cancer Activity The ability of HSP90 inhibitors to act synergistically with the selective BCL-2 inhibitor, venetoclax, was examined using HSP90 inhibitors representing six different chemical scaffolds. These included the purine-like inhibitor, MPC-0767, a resorcinol derivative, AT-13387, a geldanamycin derivative, tanespimycin, a pyrazolopyridine derivative, TAS-116, a dihydroindazolone derivative, SNX-5422, and a tropane derivative, XL888. Selecting inhibitors with such diverse chemical scaffolds increases the likelihood that any observations made are due to on-target activity, i.e. inhibition of HSP90, because any off-target effects would be expected to vary between different inhibitor molecules, and especially between different inhibitor molecules based on different chemical scaffolds.

We also sought to determine whether the HSP90 inhibitors act synergistically with the BCL-2 inhibitor, venetoclax, in different cancer types. To do this we used four different cancer cell lines representing each of the three classes of haematopoietic and lymphoid cancers, leukemias, lymphomas, and myelomas. For leukemias, we used an acute myeloid leukemia (AML) cell line, MV-4-11; for lymphomas, we used a diffuse large B cell lymphoma (DLBCL) cell line, OCI-LY-19, and a mantle cell lymphoma cell line, Z138; and for myelomas we used the multiple myeloma cell line, KMS-28.

Cells were treated with venetoclax combined with each of the six HSP90 inhibitors at the concentrations shown in Table 2.

TABLE 2

Cell lines, HSP90 inhibitors, and drug concentrations (nM) tested.

| | MV-4-11 | OCI-LY-19 | Z138 | KMS-28 |
|---|---|---|---|---|
| Venetoclax | 0.78-100 | 0.78-100 | 0.78-100 | 3.9-500 |
| MPC-0767 | 78-10000 | 78-10000 | 78-10000 | 78-10000 |
| Tanespimycin | 7.8-1000 | 78-10000 | 7.8-1000 | 78-10000 |
| TAS-116 | 7.8-1000 | 7.8-1000 | 7.8-1000 | 7.8-1000 |

TABLE 2-continued

Cell lines, HSP90 inhibitors, and drug concentrations (nM) tested.

| | MV-4-11 | OCI-LY-19 | Z138 | KMS-28 |
|---|---|---|---|---|
| AT-13387 | 7.8-1000 | 7.8-1000 | 7.8-1000 | 7.8-1000 |
| SNX-5422 | 7.8-1000 | 7.8-1000 | 7.8-1000 | 7.8-1000 |
| XL-888 | 7.8-1000 | 7.8-1000 | 7.8-1000 | 7.8-1000 |

After 72 hour treatment with the indicated drug combinations, cell viability was assessed using CellTiter-Glo. Isobologram analysis was performed to determine synergistic interactions. Briefly, normalized isobolograms were used to depict the drug interactions observed across different cell lines at a dose effect of 75% (EC75). The absolute EC75 for each single agent and drug combination was calculated using the R package DRC (Ritz et al., Dose-Response Analysis Using R. PLoS One. 2015. 10(12):e0146021; R Core Team, A language and environment for statistical computing. R Foundation for Statistical Computing, Vienna, Austria. 2017). Next, we normalized the EC75 of the drug combination with respect to corresponding single agent EC75 values. In cases when single agent treatments did not reach EC75, then the relative EC75 was used based on the projected value of the fitted drug response curve. When the relative EC75 was higher than the maximum concentration tested, we used the maximum concentration tested as the default value, to allow analysis across all drugs and conditions.

As shown in FIG. 11A-F, each of the HSP90 inhibitors demonstrated synergistic activity with venetoclax in all of the cell lines. This is evidenced in the figure by the location of each data point being below the line of additivity, which is shown in each plot as a dashed line.

These findings indicate that HSP90 inhibitors generally are able to act synergistically with venetoclax to inhibit cell viability in haematopoietic and lymphoid cancers. These data also indicate that the synergistic anti-cancer activity is due to on-target inhibition of HSP90, as opposed to off-target effects.

Example 3: BCL-2 Abundance is Predictive of Synergy Between MPC-0767 and Venetoclax in Multiple Cancers Venetoclax sensitivity has been shown to correlate with the abundance of its molecular target, BCL-2 protein (Pan et al., Selective BCL-2 inhibition by ABT-199 causes on-target cell death in acute myeloid leukemia. Cancer Discov. 2014; 4(3):362-75).

To test whether BCL-2 abundance is predictive of the synergy between HSP90 inhibitors and venetoclax observed here, we analyzed BCL-2 abundance in cell lines representing acute myeloid leukemia (MV-4-11, MOLM-16, TUR and U937), multiple myeloma (KMS-28), diffuse large B cell lymphoma (OCI-LY-19) and mantle cell lymphoma (Z138) under basal conditions using flow cytometry.

In parallel, the same cell lines representing acute myeloid leukemia, multiple myeloma, diffuse large B cell lymphoma and mantle cell lymphoma were treated with venetoclax for 72 hours and cell viability determined by CellTiter-Glo. $EC_{50}$ values were determined as described above.

Figure 12:
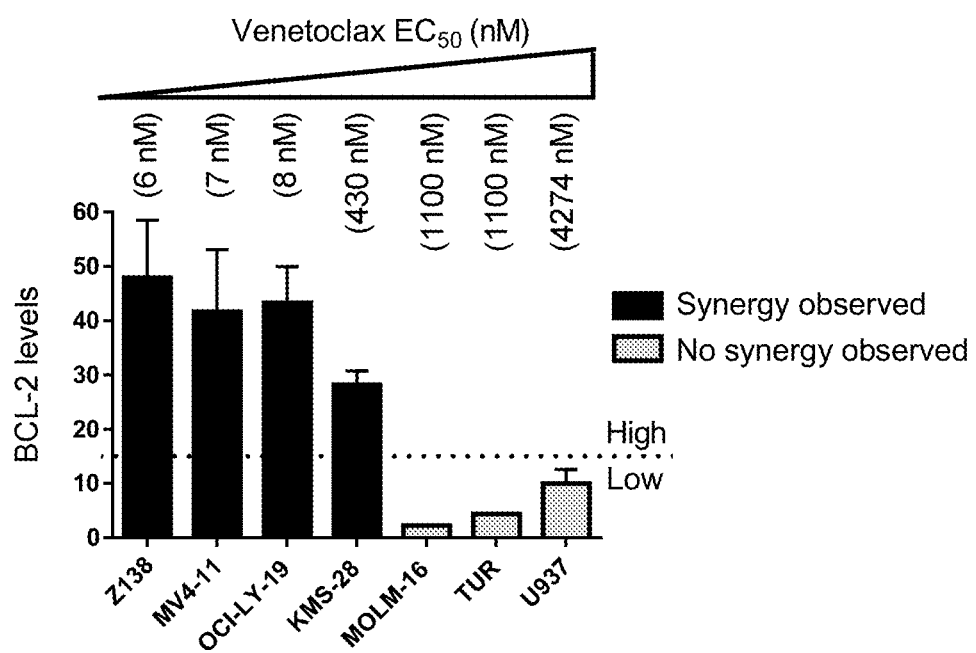
FIG. 12: Cell lines representing acute myeloid leukemia, multiple myeloma, diffuse large B cell lymphoma and mantle cell lymphoma were assayed for basal abundance of BCL-2 (Y axis) and a high/low threshold is shown by dashed line. Cell line sensitivity to venetoclax after 72 hour treatment as assessed by CellTiter-Glo (X axis) is denoted by EC50 values shown in parentheses. Following drug combination treatment of MPC-0767 and venetoclax, determination of synergy is shown by bar graphs in black (synergy observed) or grey (no synergy observed).
Figure 13A:
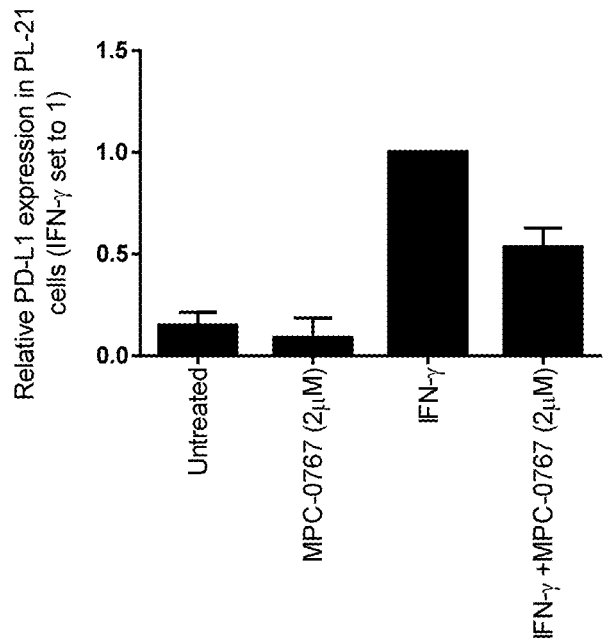
FIG. 13A-D: MPC-0767 blocks IFN-γ-induced PD-L1 expression in AML cells. A) PL-21, B) TUR, C) MOLM-14, D) MV-4-11 cells treated with MPC-0767 (2 μM), IFN-γ (50 ng/ml) or IFN-γ+MPC-0767 for 24 h before cells were harvested for assessment of PD-L1 cell surface expression.
Figure 13B:
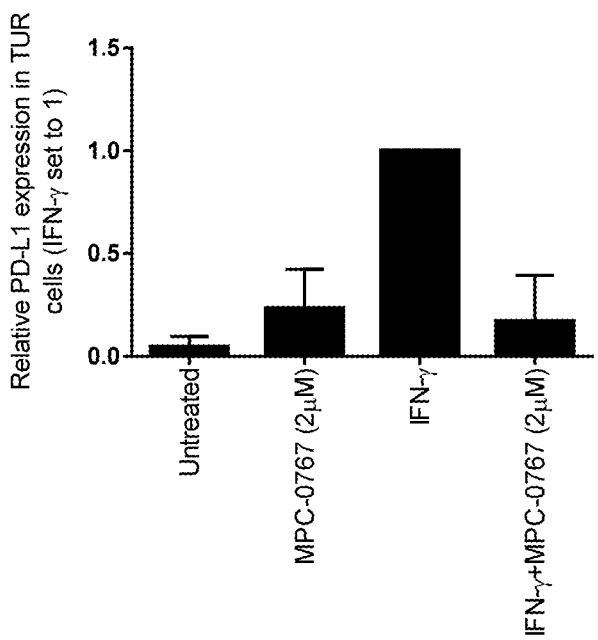
Figure 13C:
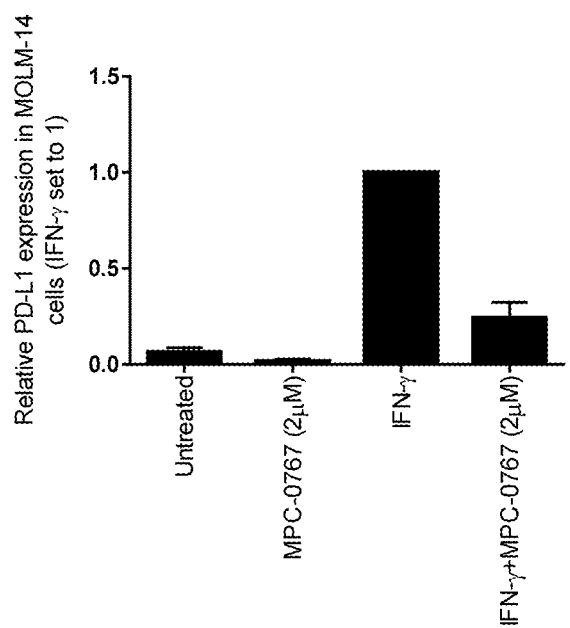
Figure 13D:
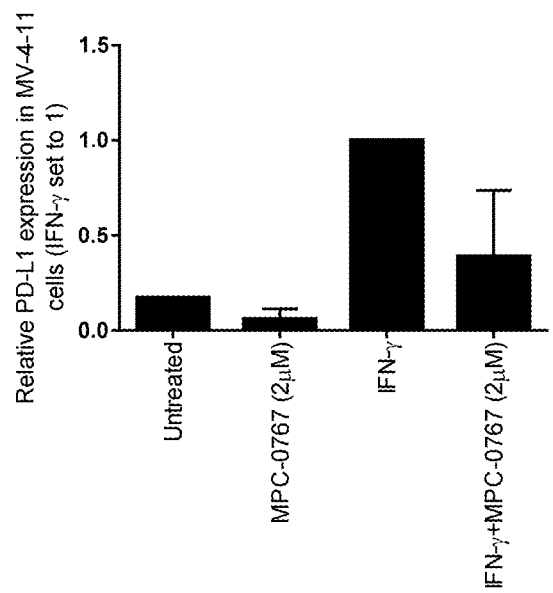

These data showed a trend between basal levels of BCL-2 and venetoclax sensitivity (FIG. 12). We next determined whether the observed HSP90 inhibitor and venetoclax synergy depended on basal BCL-2 levels. Each cell line was treated with a combination of MPC-0767 and venetoclax and viability assayed 72 hours later using CellTiter-Glo. Synergy was determined as described above. As shown in FIG. 12, synergy with MPC-0767 and venetoclax was observed in 4 out of 4 cell lines with high BCL-2 levels. In contrast, no synergy was observed in the three cell lines with low BCL-2 levels. These findings suggest that cancers with a reliance on BCL-2 may be especially susceptible to treatment with a combination of an HSP90 inhibitor and a BCL-2 pathway inhibitor.

Example 4: MPC-0767 Blocks Interferon-Induced PD-L1 Expression

The release of interferon-gamma (IFN-γ) from T-cells plays a key role in the host immune response to infections. Yet this released IFN-γ also provides a mechanism by which tumor cells can evade the immune system through induction of programmed death-ligand-1 (PD-L1).

To ascertain whether MPC-0767 can block IFN-γ-induced PD-L1 expression in AML cells, four AML cell lines harboring WT FLT3 (n=2) or FLT3-ITD (n=2) were treated with human IFN-γ (50 ng/ml) alone, MPC-0767 (2 μM) alone or the combination for 24 hours. Cells were harvested to determine PD-L1 cell surface expression by flow cytometry. Cells were also stained with a viability stain to gate on viable cells and exclude any dead cells. As shown in FIG. 13A-D, all cell lines induced PD-L1 cell surface expression in response to IFN-γ treatment (6-25 fold). While MPC-0767 alone did not significantly reduce basal PD-L1 cell surface expression, in combination with IFN-γ, MPC-0767 reduced the IFN-γ-induced PD-L1 cell surface expression in all cell lines (range: 43-83% reduction).

These data demonstrate that MPC-0767 displays immuno-modulatory activity in AML cells by blocking IFN-γ-induced PD-L1 expression.

What is claimed is:

1. A method for treating a hematopoietic or lymphoid cancer selected from a leukemia, a lymphoma and a multiple myeloma in a subject in need thereof, the method comprising administering to the subject an amount of an HSP90 inhibitor and a BCL-2 inhibitor, wherein the BCL-2 inhibitor is venetoclax and the HSP90 inhibitor is selected from MPC-0767, AT-13387, tanespimycin, TAS-116, SNX-5422, and XL-888, and pharmaceutically acceptable salts thereof.

2. The method of claim 1, wherein the cancer is characterized as positive for BCL-2 expression based on the expression of BCL-2 in a biological sample of the cancer.

3. The method of claim 2, wherein the cancer characterized as positive for BCL-2 expression is a cancer in which a biological sample from the cancer expresses BCL-2 at a level that is at least two-fold higher compared to the BCL-2 expression in a reference sample of non-cancerous tissue.

4. The method or composition of claim 3, wherein the BCL-2 expression is protein expression or gene expression.

5. The method of claim 1, wherein the amount of the HSP90 inhibitor is less than 90% of the recommended phase 2 dose of the HSP90 inhibitor.

6. The method of claim 1, wherein the cancer is a leukemia selected from acute lymphoblastic leukemia (ALL), acute myelogenous leukemia (AML), chronic lymphocytic leukemia (CLL), chronic myelogenous leukemia (CML), and acute monocytic leukemia.

7. The method of claim 6, wherein the cancer is AML.

8. The method of claim 1, wherein the cancer is a lymphoma selected from a Hodgkins and a Non-Hodgkin's lymphoma.

9. The method of claim 8, wherein the cancer is a Non-Hodgkin's B cell lymphoma, preferably selected from a diffuse large B cell lymphoma (DLBCL), Burkitt lymphoma, lymphoblastic lymphoma, and mantle cell lymphoma, and most preferably selected from a diffuse large B cell lymphoma (DLBCL) and a mantle cell lymphoma.

10. The method of claim 1, wherein the cancer is a multiple myeloma.

11. The method of claim 1, wherein the HSP90 inhibitor is MPC-0767 or tanespimycin, and pharmaceutically acceptable salts thereof.

12. The method of claim 1, wherein the subject is human.

* * * * *